US012799502B2

(12) United States Patent
Rivella et al.

(10) Patent No.: US 12,799,502 B2
(45) Date of Patent: Nov. 17, 2026

(54) COMPOSITIONS AND METHODS FOR TREATING ANEMIA

(71) Applicant: THE CHILDREN'S HOSPITAL OF PHILADELPHIA, Philadelphia, PA (US)

(72) Inventors: Stefano Rivella, Philadelphia, PA (US); Joseph Oved, Bala Cynwyd, PA (US); Carlo Castruccio Castracani, Philadelphia, PA (US)

(73) Assignee: THE CHILDREN'S HOSPITAL OF PHILADELPHIA, Philadelphia, PA (US)

(*) Notice: Subject to any disclaimer, the term of this patent is extended or adjusted under 35 U.S.C. 154(b) by 994 days.

(21) Appl. No.: 17/621,625

(22) PCT Filed: Jun. 29, 2020

(86) PCT No.: PCT/US2020/040097
§ 371 (c)(1),
(2) Date: Dec. 21, 2021

(87) PCT Pub. No.: WO2020/264488
PCT Pub. Date: Dec. 30, 2020

(65) Prior Publication Data

US 2022/0389448 A1 Dec. 8, 2022

Related U.S. Application Data

(60) Provisional application No. 62/910,723, filed on Oct. 4, 2019, provisional application No. 62/868,224, filed on Jun. 28, 2019.

(51) Int. Cl.

| | |
|---|---|
| ***C12N 15/86*** | (2006.01) |
| ***A61K 35/76*** | (2015.01) |
| ***A61K 48/00*** | (2006.01) |
| ***A61P 7/06*** | (2006.01) |

(52) U.S. Cl.
CPC .............. *C12N 15/86* (2013.01); *A61K 35/76* (2013.01); *A61K 48/0058* (2013.01); *A61P 7/06* (2018.01)

(58) Field of Classification Search
None
See application file for complete search history.

(56) References Cited

U.S. PATENT DOCUMENTS

| | | | | |
|---|---|---|---|---|
| 7,541,179 | B2 * | 6/2009 | Sadelain | C12N 15/86 435/320.1 |
| 7,901,671 | B2 | 3/2011 | Leboulch et al. | |
| 8,058,061 | B2 | 11/2011 | Sadelain et al. | |
| 9,068,199 | B2 | 6/2015 | Leboulch et al. | |
| 11,311,631 | B2 * | 4/2022 | Markovic | A61K 47/6929 |
| 11,311,632 | B2 | 4/2022 | Cornell et al. | |
| 2003/0022303 | A1 | 1/2003 | Sadelain et al. | |
| 2009/0124566 | A1 | 5/2009 | Chi et al. | |
| 2009/0156534 | A1 | 6/2009 | Lisowski et al. | |
| 2009/0274671 | A1 | 11/2009 | Sadelain et al. | |
| 2012/0009161 | A1 | 1/2012 | Leboulch et al. | |
| 2012/0039932 | A1 | 2/2012 | Allen et al. | |
| 2015/0224209 | A1 | 8/2015 | Kohn et al. | |
| 2017/0157270 | A1 | 6/2017 | Kohn et al. | |
| 2017/0173185 | A1 | 6/2017 | Sadelain et al. | |
| 2018/0008725 | A1 * | 1/2018 | Rivella | A61P 7/00 |
| 2018/0051059 | A1 | 2/2018 | Blobel et al. | |
| 2018/0363004 | A1 | 12/2018 | Heffner et al. | |
| 2021/0222200 | A1 | 7/2021 | Rivella et al. | |
| 2022/0202958 | A1 | 6/2022 | Rivella et al. | |

FOREIGN PATENT DOCUMENTS

| | | | | |
|---|---|---|---|---|
| WO | 2002/010454 | A2 * | 2/2002 | C12N 9/10 |
| WO | 2003/002155 | A1 | 1/2003 | |
| WO | 2004/083383 | A2 | 9/2004 | |
| WO | 2011/011584 | A1 | 1/2011 | |
| WO | 2013/184197 | A1 | 12/2013 | |
| WO | 2014/043131 | A1 | 3/2014 | |
| WO | 2014/108812 | A2 | 7/2014 | |
| WO | 2016/118715 | A1 | 7/2016 | |
| WO | 2017/003792 | A1 | 1/2017 | |
| WO | 2017/079591 | A2 | 5/2017 | |
| WO | 2017/191274 | A2 | 11/2017 | |
| WO | 2019/213011 | A1 | 11/2019 | |
| WO | 2020/056400 | A1 | 3/2020 | |

OTHER PUBLICATIONS

Ducamp, Sarah, and Mark D. Fleming. Blood, The Journal of the American Society of Hematology 133.1 (2019): 59-69. (Year: 2019).*
Tolar, Jakub, et al. Human gene therapy 23.2 (2012): 141-144. (Year: 2012).*
Wang, Yi-Qun, et al. Zhongguo shi yan xue ye xue za zhi 12.5 (2004): 687-693. (English abstract only) (Year: 2004).*
Deboer, Ernie, et al. The EMBO journal 7.13 (1988): 4203-4212. (Year: 1988).*
Cavazzana-Calvo, Marina, et al. Nature 467.7313 (2010): 318-322, Supplement.*
Dercksen, Marcus W., et al. Journal of clinical oncology 13.8 (1995): 1922-1932.*
Cavazzana-Calvo, Marina, et al. Nature 467.7313 (2010): 318-322, Supplement (Year: 2010).*
Dercksen, Marcus W., et al. Journal of clinical oncology 13.8 (1995): 1922-1932. (Year: 1995).*

(Continued)

*Primary Examiner* — Maria Marvich
*Assistant Examiner* — Brendan Thomas Tinsley
(74) *Attorney, Agent, or Firm* — Robert C. Netter, Jr.; Dann, Dorfman, Herrell & Skillman

(57) ABSTRACT

Methods and compositions for producing heme and treating sideroblastic anemia are disclosed.

13 Claims, 55 Drawing Sheets

Figure 1:
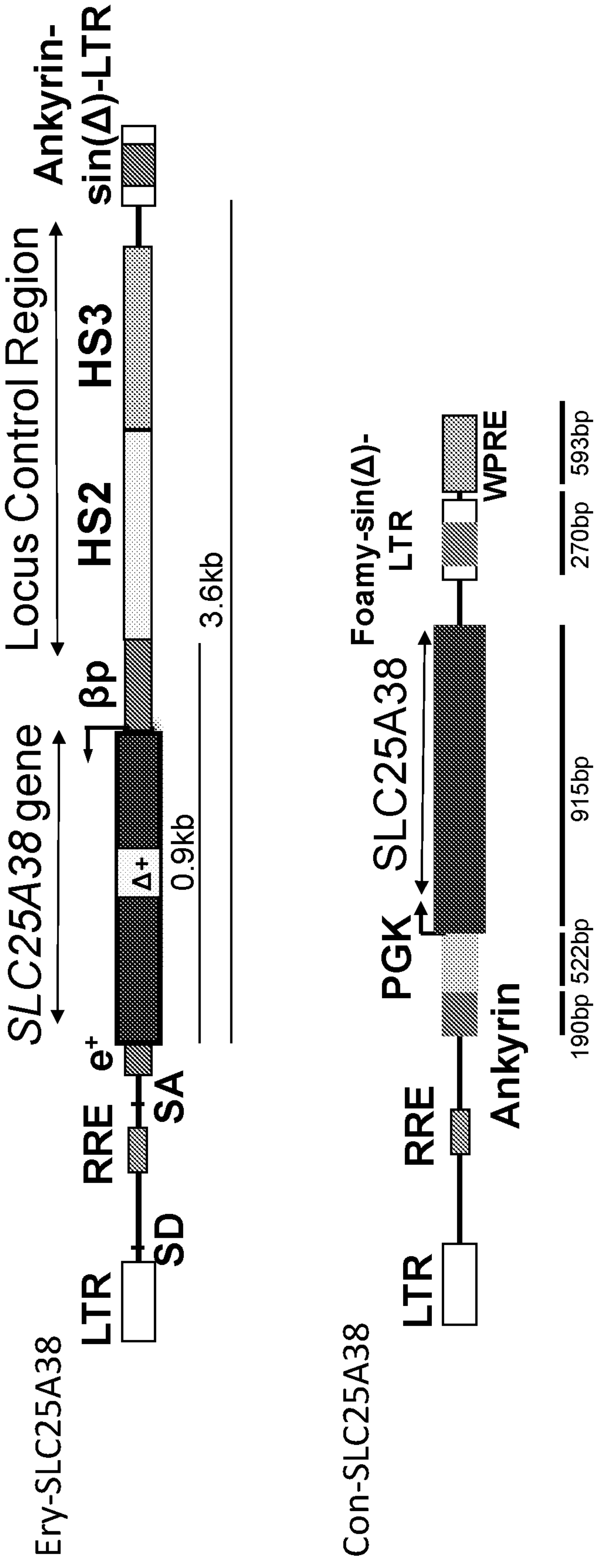

Specification includes a Sequence Listing.

(56) References Cited

OTHER PUBLICATIONS

Santoro et al., Int J Mol Sci. Dec. 12, 2024;25(24):13314 (Year: 2024).*
Oh, et al., "Lentiviral vector design using alternative RNA export elements" Retrovirology (2007) 4:38.
Mauro, et al., "A critical analysis of codon optimization in human therapeutics" Trends Mol. Med. (2014) 20(11):604-613.
Han, et al., "Fetal gene therapy of a-thalassemia in a mouse model" Proc. Natl. Acad. Sci. (2007) 104(21):9007-11.
Fraser, et al., "Each hypersensitive site of the human beta-globin locus control region confers a different developmental pattern of expression on the globin genes" Genes Dev. (1993) 7(1):106-13.
Emery, D.W., "The use of chromatin insulators to improve the expression and safety of integrating gene transfer vectors" Hum. Gene Ther. (2011) 22(6):761-74.
Dutta, et al., "PDB-101: Molecule of the Month: Hemoglobin" (2003) Protein Data Bank, available at http://doi. org/10.2210/rcsb_pdb/mom_2003_5.
Musallam, K.M., et al., "Non-transfusion-dependent thalassemias" Haematologica (2013) 98(6):833-44.
Rivella, S., "The role of ineffective erythropoiesis in non-transfusion-dependent thalassemia" Blood Rev. (2012) 26 Suppl 1:S12-5.
Ginzburg, Y., et al., "B-thalassemia: a model for elucidating the dynamic regulation of ineffective erythropoiesis and ron metabolism" Blood (2011) 118(16):4321-30.
May, C., et al., "Successful treatment of murine beta-thalassemia intermedia by transfer of the human beta-globin gene" Blood (2002) 99(6):1902-8.
May, C., et al., "Therapeutic haemoglobin synthesis in beta-thalassaemic mice expressing lentivirus-encoded human beta-globin" Nature (2000) 406(6791):82-6.
Rivella, S., et al., "A novel murine model of Cooley anemia and its rescue by lentiviral-mediated human beta-globin gene transfer" Blood (2003) 101(8):2932-9.
Breda, L., et al., "Therapeutic hemoglobin levels after gene transfer in B-thalassemia mice and in hematopoietic cells of B-thalassemia and sickle cells disease patients" PLoS One (2012) 7(3):e32345.
Pawliuk, R., et al., "Correction of sickle cell disease in transgenic mouse models by gene therapy" Science (2001) 294(5550):2368-71.
Cavazzana-Calvo, M., et al., "Transfusion independence and HMGA2 activation after gene therapy of human β-thalassaemia" Nature (2010) 467(7313):318-22.
Samakoglu, S., et al., "A genetic strategy to treat sickle cell anemia by coregulating globin transgene expression and RNA interference" Nat. Biotechnol. (2006) 24(1):89-94.
Deng, W., et al., "Reactivation of developmentally silenced globin genes by forced chromatin looping" Cell (2014) 158(4):849-860.
Negre, O., et al., "Gene Therapy of the β-Hemoglobinopathies by Lentiviral Transfer of the β(A(T87Q))-Globin Gene" Hum Gene Ther. (2016) 27(2):148-65.
Bokinni, et al., "Producing and evaluating a novel lentiviral vector for beta-thalassaemia gene therapy" BMC Proceedings (2012) 6(Suppl 4):O15.
Leboulch, P., et al., "Mutagenesis of retroviral vectors transducing human beta-globin gene and beta-globin locus control region derivatives results in stable transmission of an active transcriptional structure" EMBO J. (1994) 13(13):3065-76.
Arumugam, P., et al., "Genetic Therapy for Beta-Thalassemia: From the Bench to the Bedside" Hematology Am. Soc. Hematol. Educ. Program (2010) 2010(1):445-450.
Lisowski, et al., "Current status of globin gene therapy for the treatment of beta-thalassaemia" Br. J. Haematol. (2008) 141(3):335-45.
Guda, et al., "miRNA-embedded shRNAs for Lineage-specific BCL11A Knockdown and Hemoglobin F Induction" Molecular Therapy (2015) 23(9):1465-1474.
Fellmann, et al., "An Optimized microRNA Backbone for Effective Single-Copy RNAi" Cell Reports (2013) 5:1704-1713.
Zaiss, et al., "RNA 3' readthrough of oncoretrovirus and lentivirus: implications for vector safety and efficacy" J Virol. (2002) 76(14):7209-19.
Puthenveetil, et al., "Successful correction of the human beta-thalassemia major phenotype using a lentiviral vector" Blood (2004) 104(12):3445-53.
Wilber, et al., "Therapeutic levels of fetal hemoglobin in erythroid progeny of B-thalassemic CD34+ cells after entiviral vector-mediated gene transfer" Blood (2011) 117(10):2817-26.
Miccio, et al., "The GATA1-HS2 enhancer allows persistent and position-independent expression of a β-globin transgene" PLoS One (2011) 6(12):e27955.
Lourenco, et al., "Screening Vectors for the Treatment of ß-Globinopathies: a Quest for More Efficient Therapies" American Society of Gene & Cell Therapy, Chicago (2018) available at https://plan.core-apps.com/asgct2018/abstract/a87546bc-e7ce-4fb8-9998-d59aa67babb5.
Lourenco, et al., "HbA and HbF Simultaneous Induction by Double-Pronged Lentiviral Vector ATM1.1 Outperforms Beta-Globin-Based Gene Addition and miRNA-Based Gamma-Globin Reactivation in SCD-Derived Erythroblasts" Molecular Therapy (2019) 27(4S1):279.
Ikawa, et al., "High Levels of Transduction in CD34 Positive Cells and Toxicology Studies Using New Lentiviral Vectors for the Cure of Hemoglobinopathies" Molecular Therapy (2019) 27(4S1):285.
Lisowski, et al., "Locus control region elements HS1 and HS4 enhance the therapeutic efficacy of globin gene transfer in beta-thalassemic mice" Blood (2007) 110:4175-4178.
Rai, et al., "Gene therapy for hemoglobin disorders—a mini-review" J. Rare Dis. Res. Treat. (2016) 1(2): 25-31.
Dong, et al., "Gene therapy for hemoglobinopathies: progress and challenges" Transl. Res. (2013) 161(4):293-306.
Antoniou, M., et al., "Efficient 3'-end formation of human beta-globin mRNA in vivo requires sequences within the last intron but occurs independently of the splicing reaction" Nucleic Acids Res. (1998) 26(3):721-9.
El-Rashidi, et al., "The role of the soluble transferrin receptor in iron overload in children with chronic hemolytic anemia" Menoufia Med. J. (2013) 26(2):132-137.
Li, et al., "Trasnferrin therapy ameliorates disease in Beta-thalassemic mice" Nature Med. (2010) 16(2):177-183.
Huebers, et al., "The Physiology of Transferrin and Transferrin Receptors" Physiological Rev. (1987) 67(2):520-582.
Abelson, et al., "tRNA Splicing" J. Biol. Chem. (1998) 273(21):12685-12688.
Molecular Biology Web Book, Chapter 5: Posttranscriptional Processes, A4: Rna Splicing, obtained at https://www.web-books.com/MoBio/Free/Ch5A4.htm (2019) pp. 1-5.
Wikipedia, "Complementary DNA" accessed at https://en.wikipedia.org/wiki/Complentary DNA on Feb. 4, 2019, pp. 1-3.
Drakopoulou, et al., "Towards More Successful Gene Therapy Clinical Trials for Beta-Thalassemia" Current Molecular Med. (2013) 13:1314-1330.
Chiabrando, et al., "Heme and erythropoieis: more than a structural role" Haematologica (2014) 99(6):973-83.
Dufay, J.N., "Defining the role of Hem25 in mitochondrial function: implications for congenital sideroblastic anemia" Master of Science Thesis, Dalhousie University, Hailfax, Nova Scotia (2015) Retrieved from the internet: https://dalspace.library.dal.ca/handle/10222/58896.
Guernsey, et al., "Mutations in mitochondrial carrier family gene SLC25A38 cause nonsyndromic autosomal recessive congenital sideroblastic anemia" Nat. Genet. (2009) 41(6): 651-653.
Kannengiesser, et al., "Missense SLC25A38 variations play an important role in autosomal recessive Inherited sideroblastic anemia" Haematoloica (2011) 96(6):808-813.
Castracani, et al., "An erythroid-specific lentiviral vector improves anemia and iron metabolism in a new model of XLSA" Blood (2025) 145:98-113.
Clontech Laboratories, Inc., "pDsRed2-N1 Vector Information" (2012) available at https://www.takarabio.com/documents/Vector%20Documents/PT3604-5_121712.pdf.

(56) References Cited

OTHER PUBLICATIONS

Wang, et al., "Construction of Recombinant Vector Expressing ALAS2 gene in X-linked Sideroblastic Anemia" J. Exp. Hematol. (2004) 12(5):687-693.

* cited by examiner

```
  1 MIQNSRPSLL QPQDVGDTVE TLMLHPVIKA FLCGSISGTC STLLFQPLDL LKTRLQTLQP
 61 SDHGSRRVGM LAVLLKVVRT ESLLGLWKGM SPSIVRCVPG VGIYFGTLYS LKQYFLRGHP
121 PTALESVMLG VGSRSVAGVC MSPITVIKTR YESGKYGYES IYAALRSIYH SEGHRGLFSG
181 LTATLLRDAP FSGIYLMFYN QTKNIVPHGL WTTWLLPRWH PPSPPQNSNG SNGVDGV
```

```
  1 MIQNSRPSLL QPQDVGDTVE TLMLHPVIKA FLCGSISGTC STLLFQPLDL LKTRLQTLQP
 61 SDHGSRRVGM LAVLLKVVRT ESLLGLWKGM SPSIVRCVPG VGIYFGTLYS LKQYFLRGHP
121 PTALESVMLG VGSRSVAGVC MSPITVIKTR YESGKYGYES IYAALRSIYH SEGHRGLFSG
181 LTATLLRDAP FSGIYLMFYN QTKNIVPHDQ VDATLIPITN FSCGIFAGIL ASLVTQPADV
241 IKTHMQLYPL KFQWIGQAVT LIFKDYGLRG FFQGGIPRAL RRTLMAAMAW TVYEEMMAKM
301 GLKS
```

Figure 5A

```
atgat tcagaactca cgtccgtcgc tgctgcaacc ccaagatgtc ggagacacgg tggaaacgct
tatgttacat ccggtgatca aggctttcct gtgtggctcc atcagtggga cctgctctac
cctcctttc caacctctgg atctccttaa aacacgcctg caaaccctcc agccctcaga
tcatgggtct agacgtgttg ggatgttggc tgtactcttg aaggtggttc gcacggagag
tcttttgggc ctttggaaag ggatgtcccc ttccattgtg agatgtgtcc ctggcgttgg
aatctacttt ggcactctct actctttgaa gcagtatttc ttgcgaggcc atccccaac
cgccctggag tcagtcatgc tgggggtggg ctctcgctct gttgcagggg tctgtatgtc
acctatcact gtaatcaaga cgcgctatga gagtgggaaa tatggctatg agagtatcta
cgctgccctg aggagcatct atcacagtga ggggcaccgg ggcctcttca gtggcctgac
agcaactctc cttcgagatg cgcccttctc aggaatctac ctgatgtttt acaaccagac
caaaaatata gtgcctcatg gactatggac tacgtggctt cttccaaggt ggcatcccc
gagccctccg cagaactcta atggcagcaa tggcgtggac ggtgtatga
```

```
atgat tcagaactca cgtccgtcgc tgctgcaacc ccaagatgtc ggagacacgg tggaaacgct
tatgttacat ccggtgatca aggctttcct gtgtggctcc atcagtggga cctgctctac
cctcctttc caacctctgg atctccttaa aacacgcctg caaaccctcc agccctcaga
tcatgggtct agacgtgttg ggatgttggc tgtactcttg aaggtggttc gcacggagag
tcttttgggc ctttggaaag ggatgtcccc ttccattgtg agatgtgtcc ctggcgttgg
aatctacttt ggcactctct actctttgaa gcagtatttc ttgcgaggcc atccccaac
cgccctggag tcagtcatgc tgggggtggg ctctcgctct gttgcagggg tctgtatgtc
acctatcact gtaatcaaga cgcgctatga gagtgggaaa tatggctatg agagtatcta
cgctgccctg aggagcatct atcacagtga ggggcaccgg ggcctcttca gtggcctgac
agcaactctc cttcgagatg cgcccttctc aggaatctac ctgatgtttt acaaccagac
caaaaatata gtgcctcatg accaggtgga tgcaaccctt attcctatta caaatttcag
ctgtgggata tttgctggta ttctggcctc actggtaact caacctgcgg atgttatcaa
aactcatatg cagctttatc cactgaagtt tcaatggatt ggccaagcag tgacacttat
tttcaaagac tatggactac gtggcttctt ccaaggtggc atcccccgag ccctccgcag
aactctaatg gcagcaatgg cgtggacggt gtatgaagag atgatggcca agatgggcct
gaagtcctga
```

Figure 5B

```
  1 MVTAAMLLQC CPVLARGPTS LLGKVVKTHQ FLFGIGRCPI LATQGPNCSQ IHLKATKAGG
 61 DSPSWAKGHC PFMLSELQDG KSKIVQKAAP EVQEDVKAFK TDLPSSLVSV SLRKPFSGPQ
121 EQEQISGKVT HLIQNNMPGN YVFSYDQFFR DKIMEKKQDH TYRVFKTVNR WADAYPFAQH
181 FSEASVASKD VSVWCSNDYL GMSRHPQVLQ ATQETLQRHG AGAGGTRNIS GTSKFHVELE
241 QELAELHQKD SALLFSSCFV ANDSTLFTLA KILPGCEIYS DAGNHASMIQ GIRNSGAAKF
301 VFRHNDPDHL KKLLEKSNPK IPKIVAFETV HSMDGAICPL EELCDVSHQY GALTFVDEVH
361 AVGLYGSRGA GIGERDGIMH KIDIISGTLG KAFGCVGGYI ASTRDLVDMV RSYAAGFIFT
421 TSLPPMVLSG ALESVRLLKG EEGQALRRAH QRNVKHMRQL LMDRGLPVIP CPSHIIPIRV
481 GNAALNSKLC DLLLSKHGIY VQAINYPTVP RGEELLRLAP SPHHSPQMME DFVEKLLLAW
541 TAVGLPLQDV SVAACNFCRR PVHFELMSEW ERSYFGNMGP QYVTTYA
```

Figure 5C

```
atggtgact gcagccatgc tgctacagtg ctgcccagtg cttgcccggg gccccacaag cctcctaggc
aaggtggtta agactcacca gttcctgttt ggtattggac gctgtcccat cctggctacc
caaggaccaa actgttctca aatccacctt aaggcaacaa aggctggagg agattctcca
tcttgggcga agggccactg tcccttcatg ctgtcggaac tccaggatgg gaagagcaag
attgtgcaga aggcagcccc agaagtccag gaagatgtga aggctttcaa gacagatctg
cctagctccc tggtctcagt cagcctaagg aagccatttt ccggtcccca ggagcaggag
cagatctctg ggaaggtcac acacctgatt cagaacaata tgcctggaaa ctatgtcttc
agttatgacc agtttttcag ggacaagatc atggagaaga aacaggatca cacctaccgt
gtgttcaaga ctgtgaaccg ctgggctgat gcatatccct ttgcccaaca tttctctgag
gcatctgtgg cctcaaagga tgtgtccgtc tggtgtagta atgattacct gggcatgagc
cgacaccctc aggtcttgca agccacacag gagaccctgc agcgtcatgg tgctggagct
ggtggcaccc gcaacatctc aggcaccagt aagtttcatg tggagcttga gcaggagctg
gctgagctgc accagaagga ctcagccctg ctcttctcct cctgctttgt tgccaatgac
tctactctct tcaccttggc caagatcctg ccagggtgcg agatttactc agacgcaggc
aaccatgctt ccatgatcca aggtatccgt aacagtggag cagccaagtt tgtcttcagg
cacaatgacc ctgaccacct aaagaaactt ctagagaagt ctaaccctaa gatacccaaa
attgtggcct ttgagactgt ccactccatg gatggtgcca tctgtcccct cgaggagttg
tgtgatgtgt cccaccagta tggggccctg accttcgtgg atgaggtcca tgctgtagga
ctgtatgggt cccggggcgc tgggattggg gagcgtgatg gaattatgca taagattgac
atcatctctg gaactcttgg caaggccttt ggctgtgtgg gcggctacat tgccagcacc
cgtgacttgg tggacatggt gcgctcctat gctgcaggct tcatctttac cacttctctg
ccccccatgg tgctctctgg agctctagaa tctgtgcggc tgctcaaggg agaggagggc
caagccctga ggcgagccca ccagcgcaat gtcaagcaca tgcgccagct actcatggac
aggggccttc ctgtcatccc ctgccccagc cacatcatcc ccatccgggt gggcaatgca
gcactcaaca gcaagctctg tgatctcctg ctctccaagc atggcatcta tgtgcaggcc
atcaactacc caactgtccc ccggggtgaa gagctcctgc gcttggcacc ctcccccac
cacagccctc agatgatgga agattttgtg gagaagctgc tgctggcttg gactgcggtg
gggctgcccc tccaggatgt gtctgtggct gcctgcaatt tctgtcgccg tcctgtacac
tttgagctca tgagtgagtg ggaacgttcc tacttcggga acatggggcc ccagtatgtc
accacctatg cctga
```

Figure 5D ctgtcagaccaagtttactcatatatactttagattgatttaaaacttca 50
pBSSK+ plasmid tttttaatttaaaaggatctaggtgaagatcctttttgataatctcatga 100
pBSSK+ plasmid ccaaaatcccttaacgtgagttttcgttccactgagcgtcagaccccgta 150
pBSSK+ plasmid gaaaagatcaaaggatcttcttgagatcctttttttctgcgcgtaatctg 200
pBSSK+ plasmid ctgcttgcaaacaaaaaaaccaccgctaccagcggtggtttgtttgccgg 250
pBSSK+ plasmid atcaagagctaccaactctttttccgaaggtaactggcttcagcagagcg 300
pBSSK+ plasmid cagataccaaatactgtccttctagtgtagccgtagttaggccaccactt 350
pBSSK+ plasmid caagaactctgtagcaccgcctacatacctcgctctgctaatcctgttac 400
pBSSK+ plasmid cagtggctgctgccagtggcgataagtcgtgtcttaccgggttggactca 450
pBSSK+ plasmid

FIG. 6

PcsI agacgatagttaccggataaggcgcagcggtcgggctgaacggggggttc 500 pBSSK+ plasmid gtgcacacagcccagcttggagcgaacgacctacaccgaactgagatacc 550 pBSSK+ plasmid tacagcgtgagctatgagaaagcgccacgcttcccgaagggagaaaggcg 600 pBSSK+ plasmid

BssSI gacaggtatccggtaagcggcagggtcggaacaggagagcgcacgaggga 650 pBSSK+ plasmid gcttccagggggaaacgcctggtatctttatagtcctgtcgggtttcgcc 700 pBSSK+ plasmid

DrdI acctctgacttgagcgtcgatttttgtgatgctcgtcaggggggcggagc 750 pBSSK+ plasmid

3' DrdI Site ctatggaaaaacgccagcaacgcggcctttttacggttcctggccttttg 800 pBSSK+ plasmid

FIG. 6 (Cont'd)

PciI
AflIII ctggcctttgctcacatgttctttcctgcgttatcccctgattctgtgg 850 pBSSK+ plasmid

PcsI ataaccgtattaccgcctttgagtgagctgataccgctcgccgcagccga 900 pBSSK+ plasmid acgaccgagcgcagcgagtcagtgagcgaggaagcggaagagcgcccaat 950 pBSSK+ plasmid acgcaaaccgcctctccccgcgcgttggccgattcattaatgcagctggc 1000 pBSSK+ plasmid acgacaggtttcccgactggaaagcgggcagtgagcgcaacgcaattaat 1050 pBSSK+ plasmid gtgagttagctcactcattaggcaccccaggctttacactttatgcttcc 1100 pBSSK+ plasmid ggctcgtatgttgtgtggaattgtgagcggataacaatttcacacaggaa 1150 pBSSK+ plasmid

BssHII acagctatgaccatgattacgccaagcgcgcaattaaccctcactaaagg 1200 pBSSK+ plasmid

FIG. 6 (cont'd)

gaacaaaagctggagctgcaagcttggccattgcatacgttgtatccata 1250 pBSSK+ plasmid CMV promoter

BsrGI tcataatatgtacatttatattggctcatgtccaacattaccgccatgtt 1300

CMV promoter

HincII gacattgattattgactagttattaatagtaatcaattacggggtcatta 1350

CMV promoter gttcatagcccatatatggagttccgcgttacataacttacggtaaatgg 1400

CMV promoter cccgcctggctgaccgcccaacgacccccgcccattgacgtcaataatga 1450

CMV promoter cgtatgttcccatagtaacgccaatagggactttccattgacgtcaatgg 1500

CMV promoter gtggagtatttacggtaaactgcccacttggcagtacatcaagtgtatca 1550

CMV promoter tatgccaagtacgccccctattgacgtcaatgacggtaaatggcccgcct 1600

CMV promoter ggcattatgcccagtacatgaccttatgggactttcctacttggcagtac 1650

CMV promoter

FIG. 6 (Cont'd)

gtgtgtgcccgtctgttgtgtgactctggtaactagagatccctcagacc 2050

5' LTR:U5

HIV

KasI
NarI
SfoI
PluTI cttttagtcagtgtggaaaatctctagcagtggcgcccgaacagggacct 2100

5' LTR:U5

HIV

Primer binding site partial Gag region gaaagcgaaagggaaaccagagctctctcgacgcaggactcggcttgctg 2150

HIV partial Gag region

BssHII aagcgcgcacggcaagaggcgaggggcggcgactggtgagtacgccaaaa 2200

HIV partial Gag region attttgactagcggaggctagaaggagagagatgggtgcgagagcgtcag 2250

HIV partial Gag region

FIG. 6 (Cont'd)

XmnI tattaagcgggggagaattagatcgcgatgggaaaaaattcggttaaggc 2300

HIV partial Gag region caggggggaaagaaaaaatataaattaaaacatatagtatgggcaagcagg 2350

HIV partial Gag region gagctagaacgattcgcagttaatcctggcctgttagaaacatcagaagg 2400

HIV partial Gag region ctgtagacaaatactgggacagctacaaccatcccttcagacaggatcag 2450

HIV partial Gag region aagaacttagatcattatataatacagtagcaaccctctattgtgtgcat 2500

HIV partial Gag region caaaggatagagataaaagacaccaaggaagctttagacaagatagagga 2550

HIV partial Gag region

FIG. 6 (Cont'd)

agaacaatttgctgagggctattgaggcgcaacagcatctgttgcaactc 2900

HIV partial Tet region acagtctggggcatcaagcagctccaggcaagaatcctggctgtggaaag 2950

HIV partial Tet region atacctaaaggatcaacagctcctggggatttggggttgctctggaaaac 3000

HIV partial Tet region

AleI tcatttgcaccactgctgtgccttggaatgctagttggagtaataaatct 3050

HIV partial Tet region ctggaacagatttggaatcacacgacctggatggagtgggacagagaaat 3100

HIV partial Tet region taacaattacacaagcttaatacactccttaattgaagaatcgcaaaacc 3150

HIV partial Tet region agcaagaaaagaatgaacaagaattattggaattagataaatgggcaagt 3200

HIV partial Tet region

FIG. 6 (Cont'd)

ttgtggaattggtttaacataacaaattggctgtggtatataaaattatt 3250

HIV partial Tet region cataatgatagtaggaggcttggtaggtttaagaatagtttttgctgtac 3300

HIV partial Tet region tttctatagtgaatagagttaggcagggatattcaccattatcgtttcag 3350

HIV partial Tet region acccacctcccaaccccgaggggacccgacaggcccgaaggaatagaaga 3400

HIV partial Tet region agaaggtggagagagagacagagacagatccattcgattagtgaacggat 3450

HIV partial Tet region

HincII ctcgacggtatcggttaacttttaaaagaaaaggggggattggggggtac 3500

HIV cPPT or FLAP agtgcaggggaaagaatagtagacataatagcaacagacatacaaactaa 3550

HIV cPPT or FLAP

FIG. 6 (Cont'd)

agaattacaaaaacaaattacaaaaattcaaaattttatCGATAAGCTTG 3600

HIV cPPT or FLAP

GGAGTTCCGCGTGTTGGGGGTGGACCATCCTCTAGGTATTGAATAAGAAA 3650

AATGAAGTTAAGGTGGTTGATGGTAACACTATGCTAATAACTGCAGAGCC 3700

AGAAGCACCATAAGGGACATGATAAGGGAGCCAGCAGACCTCTGATCTCT 3750

TCCTGAATGCTAATCTTAAACATCCTGAGGAAGAATGGGACTTCCATTTG 3800

EcoNI

GGGTGGGCCTATGATAGGGTAATAAGACAGTAGTGAATATCAAGCTACAA 3850

AAAGCCCCCTTTCAAATTCTTCTCAGTCCTAACTTTTCATACTAAGCCCA 3900

PfoI

GTCCTTCCAAAGCAGACTGTGAAAGAGTGATAGTTCCGGGAGACTAGCAC 3950

TGCAGATTCCGGGTCACTGTGAGTGGGGGAGGCAGGGAAGAAGGGCTCAC 4000

AGGACAGTCAAACCATGCCCCCTGTTTTTCCTTCTTCAAGTAGACCTCTA 4050

TAAGACAACAGAGACAACTAAGGCTGAGTGGCCAGGCGAGGAGAAACCAT 4100

CTCGCCGTAAAACATGGAAGGAACACTTCAGGGGAAAGGTGGTATCTCTA 4150

FIG. 6 (Cont'd)

AGCAAGAGAACTGAGTGGAGTCAAGGCTGAGAGATGCAGGATAAGCAAAT 4200

GGGTAGTGAAAAGACATTCATGAGGACAGCTAAAACAATAAGTAATGTAA 4250

AATACAGCATAGCAAAACTTTAACCTCCAAATCAAGCCTCTACTTGAATC 4300

CTTTTCTGAGGGATGAATAAGGCATAGGCATCAGGGGCTGTTGCCAATGT 4350

GCATTAGCTGTTTGCAGCCTCACCTTCTTTCATGGAGTTTAAGATATAGT 4400

GTATTTTCCCAAGGTTTGAACTAGCTCTTCATTTCTTTATGTTTTAAATG 4450

SwaI

CACTGACCTCCCACATTCCCTTTTTAGTAAAATATTCAGAAATAATTTAA 4500

ATACATCATTGCAATGAAAATAAATGTTTTTTATTAGGCAGAATCCAGAT 4550 beta-globin 3' UTR polyA

GCTCAAGGCCCTTCATAATATCCCCCAGTTTAGTAGTTGGACTTAGGGAA 4600 beta-globin 3' UTR

CAAAGGAACCTTTAATAGAAATTGGACAGCAAGAAAGCGAGCTTAGTGAT 4650 beta-globin 3' UTR exon 3

ACTTGTGGGCCAGGGCATTAGCCACACCAGCCACCACTTTCTGATAGGCA 4700 exon 3

FIG. 6 (Cont'd)

EcoRI

GCCTGCACTGGTGGGGTGAATTCTTTGCCAAAGTGATGGGCCAGCACACA 4750 exon 3

BstXI

GACCAGCACGTTGCCCAGGAGCTGTGGGAGGAAGATAAGAGGTATGAACA 4800 exon 3

TGATTAGCAAAAGGGCCTAGCTTGGACTCAGAATAATCCAGCCTTATCCC 4850

AACCATAAAATAAAAGCAGAATGGTAGCTGGATTGTAGCTGCTATTAGCA 4900

ATATGAAACCTCTTACATCAGTTACAATTTATATGCAGAAATATTTATAT 4950

GCAGAAATATTGCTATTGCCTTAACCCAGAAATTATCACTGTTATTCTTT 5000

AGAATGGTGCAAAGAGGCATGATACATTGTATCATTATTGCCCTGAAAGA 5050

AAGAGATTAGGGAAAGTATTAGAAATAAGATAAACAAAAAAGTATATTAA 5100

AAGAAGAAAGCATTTTTTAAAATTACAAATGCAAAATTACCCTGATTTGG 5150

BsrGI

TCAATATGTGTACACATATTAAAACATTACACTTTAACCCATAAATATGT 5200 intron 2 delete

FIG. 6 (Cont'd)

ATAATGATTATGTATCAATTAAAAATAAAAGAAAATAAAGTAGGGAGATT 5250 intron 2 delete

TstI TstI'

ATGAATATGCAAATAAGCACACATATATTCCAAATAGTAATGTACTAGGC 5300 intron 2 delete

AGACTGTGTAAAGTTTTTTTTTAAGTTACTTAATGTATCTCAGAGATATT 5350 intron 2 delete

TCCTTTTGTTATACACAATGTTAAGGCATTAAGTATAATAGTAAAAATTG 5400 intron 2 delete

MfeI

CGGAGAAGAAAAAAAAAGAAAGCAAGAATTAAACAAAAGAAAACAATTGT 5450 intron 2 delete

TATGAACAGCAAATAAAAGAAACTAAAACGATCCTGAGACTTCCACACTG 5500 intron 2 delete

ATGCAATCATTCGTCTGTTTCCCATTCTAAACTGTACCCTGTTACTTCTC 5550 intron 2 delete

CCCTTCCTATGACATGAACTTAACCATAGAAAAGAAGGGAAAGAAAACA 5600

FIG. 6 (Cont'd)

PmlI

TCAAGGGTCCCATAGACTCACCCTGAAGTTCTCAGGATCCACGTGCAGCT 5650 exon 2

TGTCACAGTGCAGCTCACTCActgTGGCAAAGGTGCCCTTGAGGTTGTCC 5700 exon 2

AGGTGAGCCAGGCCATCACTAAAGGCACCGAGCACTTTCTTGCCATGAGC 5750 exon 2

CTTCACCTTAGGGTTGCCCATAACAGCATCAGGAGTGGACAGATCCCCAA 5800 exon 2

AGGACTCAAAGAACCTCTGGGTCCAAGGGTAGACCACCAGCAGCCTAAGG 5850 exon 2

GTGGGAAAATAGACCAATAGGCAGAGAGAGTCAGTGCCTATCAGAAACCC 5900

AAGAGTCTTCTCTGTCTCCACATGCCCAGTTTCTATTGGTCTCCTTAAAC 5950

BspMI

CTGTCTTGTAACCTTGATACCAACCTGCCCAGGGCCTCACCACCAACTTC 6000 exon 1

PasI

ATCCACGTTCACCTTGCCCCACAGGGCAGTAACGGCAGACTTCTCCTCAG 6050 exon 1

FIG. 6 (Cont'd)

AleI AleI

GAGTCAGGTGCACCATGGTGTCTGTTTGAGGTTGCTAGTGAACACAGTTG 6100 exon 1 | beta globin 5' UTR

TGTCAGAAGCAAATGTAAGCAATAGATGGCTCTGCCCTGACTTTTATGCC 6150 beta globin 5' UTR

AvrII

CAGCCCTGGCTCCTGCCCTCCCTGCTCCTGGGAGTAGATTGGCCAACCCT 6200 beta globin 5' UTR

DraIII

AGGGTGTGGCTCCACAGGGTGAGGTCTAAGTGATGACAGCCGTACCTGTC 6250 beta globin 5' UTR | beta ...moter

CTTGGCTCTTCTGGCACTGGCTTAGGAGTTGGACTTCAAACCCTCAGCCC 6300 beta globin promoter

TCCCTCTAAGATATATCTCTTGGCCCCATACCATCAGTACAAATTGCTAC 6350 beta globin promoter

SnaBI

TAAAAACATCCTCCTTTGCAAGTGTATTTACGTAATATTTGGAATCACAG 6400 beta globin promoter

CTTGGTAAGCATATTGAAGATCGTTTTCCCAATTTTCTTATTACACAAAT 6450 beta globin promoter

FIG. 6 (Cont'd)

AAGAAATTGATGCACTAAAAGTGGAAGAGTTTTGTCTACCATAATTCAGC 6500 beta globin promoter

BsmBI

TTTGGGATATGTAGATGGATCTCTTCCTGCGTCTCCAGAATATGCAAAAT 6550 beta globin promoter

ACTTACAGGACAGAATGGATGAAAACTCTACCTCAGTTCTAAGCATATCT 6600 beta globin promoter

TCTCCTTATTTGGATTAAAACCTTCTGGTAAGAAAAGAAAAAAAATATAT 6650 beta globin promoter

NsiI

ATATATATGTGTATATATACACACATACATATACATATATATGCATTCAT 6700 beta globin promoter

TTGTTGTTGTTTTTCTTAATTTGCTCATGGTATATGTGTATATATATATA 6750 beta globin promoter

XbaI

TATATATTCAGGAAATAATATATTctagactcaagcctcattcagacact 6800

LCR

HS1

FIG. 6 (Cont'd)

DrdI agtgtcaccagtctcctcatatacctattgtattttcttcttcttgctgg 6850

LCR

HS1 tttagtcatgttttctgggagcttaggggcttattttattttgttttgtt 6900

LCR

HS1 ttctaatcaacagagatgggcaaacccattatttttttctttagacttgg 6950

LCR

HS1 gatggtgatagctgggcagcgtcagaaactgtgtgtggatatagataaga 7000

LCR

HS1

BlpI gctcaggactatgctgagctgtgatgagggaggggcctagctaaaggcag 7050

LCR

HS1 tgagagtcagaatgctcctgctattgccttctcagtccccacgcttggtt 7100

LCR

HS1

FIG. 6 (Cont'd)

tctacacaagtagatacatagaaaaggctataggttagtgtttgagagtc 7150

LCR

HS1 ctgcatgattagttgctcagaaatgcccgataaatatgttatgtgtgttt 7200

LCR

HS1 atgtatatatatgtttatatatatatatatgtgtgtgtgtgtgtgtgtg 7250

LCR

HS1

BsaBI tgtgttgtgtttacaaatatgtgattatcatcaaaacgtgagggctaaag 7300

LCR

HS1

AvrII XbaI tgaccagataacttgcaagtcctaggataccaggaaatCTAGAATATGTC 7350

HS2

LCR

HS1

ACATTCTGTCTCAGGCATCCATTTTCTTTATGATGCCGTTTGAGGTGGAG 7400

HS2

LCR

FIG. 6 (Cont'd)

TTTTAGTCAGGTGGTCAGCTTCTCCTTTTTTTTGCCATCTGCCCTGTAAG 7450

HS2

LCR

CATCCTGCTGGGGACCCAGATAGGAGTCATCACTCTAGGCTGAGAACATC 7500

HS2

LCR

TGGGCACACACCCTAAGCCTCAGCATGACTCATCATGACTCAGCATTGCT 7550

HS2

LCR

GTGCTTGAGCCAGAAGGTTTGCTTAGAAGGTTACACAGAACCAGAAGGCG 7600

HS2

LCR

GGGGTGGGGCACTGACCCCGACAGGGGCCTGGCCAGAACTGCTCATGCTT 7650

HS2

LCR

GGACTATGGGAGGTCACTAATGGAGACACACAGAAATGTAACAGGAACTA 7700

HS2

LCR

AGGAAAAACTGAAGCTTATTTAATCAGAGATGAGATGCTGGAAGGGATAG 7750

HS2

LCR

FIG. 6 (Cont'd)

BlpI

AGGGAGCTGAGCTTGTAAAAAGTATAGTAATCATTCAGCAAATGGTTTTG 7800

HS2

LCR

BspMI

AAGCACCTGCTGGATGCTAAACACTATTTTCAGTGCTTGAATCATAAATA 7850

HS2

LCR

PciI
AflIII

AGAATAAAACATGTATCTTATTCCCCACAAGAGTCCAAGTAAAAAATAAC 7900

HS2

LCR

AGTTAATTATAATGTGCTCTGTCCCCCAGGCTGGAGTGCAGTGGCACGAT 7950

HS2

LCR

CTCAGCTCACTGCAACCTCCGCCTCCCGGGTTCAAGCAATTCTCCTGCCT 8000

HS2

XmaI...ite

LCR

FIG. 6 (Cont'd)

GTGCCTCCCCCACCTTTCCCATGTCTGCCCTCTACTCATGGTCTATCTCT 8650
LCR
HS3

CCTGGCTCCTGGGAGTCATGGACTCCACCCAGCACCACCAACCTGACCTA 8700
LCR
HS3

PspOMI
ApaI
ACCACCTATCTGAGCCTGCCAGCCTATAACCCATCTGGGCCCTGATAGCT 8750
LCR
HS3

GGTGGCCAGCCCTGACCCCACCCCACCCTCCCTGGAACCTCTGATAGACA 8800
LCR
HS3

CATCTGGCACACCAGCTCGCAAAGTCACCGTGAGGGTCTTGTGTTTGCTG 8850
LCR
HS3

AGTCAAAATTCCTTGAAATCCAAGTCCTTAGAGACTCCTGCTCCCAAATT 8900
LCR
HS3

TACAGTCATAGACTTCTTCATGGCTGTCTCCTTTATCCACAGAATGATTC 8950
LCR
HS3

FIG. 6 (Cont'd)

AGTAGTAGATTTTATCATCCATTAATCCTTCCCTCTCCTCTCTTACTCAT 9250

LCR

HS3

CCCATCACGTATGCCTCTTAATTTTCCCTTACCTATAATAAGAGTTATTC 9300

LCR

HS3

CTCTTATTATATTCTTCTTATAGTGATTCTGGATATTAAAGTGGGAATGA 9350

LCR

HS3

XmnI

GGGGCAGGCCACTAACGAAGAAGATGTTTCTCAAAGAAGCCATTCTCCCC 9400

LCR

HS3

ACATAGATCATCTCAGCAGGGTTCAGGAAGATAAAGGAGGATCAAGGTCG 9450

LCR

HS3

FIG. 6 (Cont'd)

aaaagagaaactgaggctcagagaagggtggggactttctcagtatgaca 9750
LCR
Bluebird HS4 - corrected BclI AhdI
tggaaatgatcaggcttggattcaaagctcctgactttctgtctagtgta 9800
LCR
Bluebird HS4 - corrected tgtgcagtgagccccttttcctctaactgaaagaaggaaaaaaaaatgga 9850
LCR
Bluebird HS4 - corrected acccaaaatattctacatagtttccatgtcacagccagggctgggcagtc 9900
LCR
Bluebird HS4 - corrected SwaI NsiI
tcctgttatttcttttaaaataaatatatcatttaaatgcataaataagc 9950
LCR
Bluebird HS4 - corrected aaaccctgctcgggaatgggagggagagtctctggagtccaccccttctc 10000
LCR
Bluebird HS4 - corrected

FIG. 6 (Cont'd)

ggccctggctctgcagatagtgctatcaaagccctgacagagccctgccc 10050

LCR

Bluebird HS4 - corrected attgctgggccttggagtgagtcagcctagtagagaggcagggcaagcca 10100

LCR

Bluebird HS4 - corrected tctcatagctgctgagtgggagagagaaaagggctcattgtctataaact 10150

LCR

Bluebird HS4 - corrected caggtcatggctattcttattctcacactaagaaaaagaatgagatgtct 10200

LCR

Bluebird HS4 - corrected acatataccctgcgtcccctcttgtgtactggggtccccaagagctctct 10250

LCR

Bluebird HS4 - corrected aaaagtgatggcaaagtcattgcgctagatgccatcccatctattataaa 10300

LCR

Bluebird HS4 - corrected

BspMI cctgcatttgtctccacacaccagtcatggacaataaccctcctcccagg 10350

LCR

Bluebird HS4 - corrected

FIG. 6 (Cont'd)

acctctggattacaaaatttgtgaaagattgactggtattcttaactatg 11250

WPRE ttgctccttttacgctatgtggatacgctgctttaatgcctttgtatcat 11300

WPRE gctattgcttcccgtatggctttcattttctcctccttgtataaatcctg 11350

WPRE gttgctgtctctttatgaggagttgtggcccgttgtcaggcaacgtggcg 11400

WPRE tggtgtgcactgtgtttgctgacgcaacccccactggttggggcattgcc 11450

WPRE

PfoI accacctgtcagctcctttccgggactttcgctttccccctccctattgc 11500

WPRE cacggcggaactcatcgccgcctgccttgcccgctgctggacaggggctc 11550

WPRE ggctgttgggcactgacaattccgtggtgttgtcggggaagctgacgtcc 11600

WPRE tttccatggctgctcgcctgtgttgccacctggattctgcgcgggacgtc 11650

WPRE

FIG. 6 (Cont'd)

ATTCTATTCTGGGGGGTGGGGTGGGGCAGGACAGCAAGGGGGAGGATTGG 12000 bGH_PA_terminator

SphI

GAAGACAATAGCAGGCATGCTGGGGATGCGGTGGGCTCTATGGCTTCTGA 12050 bGH_PA_terminator

XhoI XhoI

GGAAAGAACCAGCTGGGGCTCGAGATCCACTAGTTCTAGCCTCGAGGCTA 12100

NotI SacII

GAGCGGCCGCCACCGCGGtagtagttcatgtcatcttattattcagtatt 12150

SacI...ite SV40 OriR + pA tataacttgcaaagaaatgaatatcagagagtgagaggaacttgtttatt 12200

SV40 OriR + pA gcagcttataatggttacaaataaagcaatagcatcacaaatttcacaaa 12250

SV40 OriR + pA taaagcatttttttcactgcattctagttgtggtttgtccaaactcatca 12300

SV40 OriR + pA atgtatcttatcatgtctggctctagctatcccgcccctaactccgccca 12350

SV40 OriR + pA

FIG. 6 (Cont'd)

BplI'
BplI gttccgcccattctccgccccatggctgactaattttttttatttatgca 12400

SV40 OriR + pA

SfiI
BplI'
BplI gaggccgaggccgcctcggcctctgagctattccagaagtagtgaggagg 12450

SfiI Cut Site

SV40 OriR + pA

StuI
AvrII
BsmBI ctttttggAGGCCTaggcttttgcgtcgagacgtacccaattcgcccta 12500

SV40 OriR + pA

BssHII tagtgagtcgtattacgcgcgctcactggccgtcgttttacaacgtcgtg 12550

SV40 OriR + pA actgggaaaaccctggcgttacccaacttaatcgccttgcagcacatccc 12600

SV40 OriR + pA

PvuI cctttcgccagctggcgtaatagcgaagaggcccgcaccgatcgcccttc 12650

SV40 OriR + pA

FIG. 6 (Cont'd)

FspI ccaacagttgcgcagcctgaatggcgaatggcgcgacgcgccctgtagcg 12700

SV40 OriR + pA gcgcattaagcgcggcgggtgtggtggttacgcgcagcgtgaccgctaca 12750

SV40 OriR + pA cttgccagcgccctagcgcccgctcctttcgctttcttcccttcctttct 12800

SV40 OriR + pA

NgoMIV
NaeI cgccacgttcgccggctttccccgtcaagctctaaatcgggggctccctt 12850

SV40 OriR + pA tagggttccgatttagtgctttacggcacctcgaccccaaaaaacttgat 12900

SV40 OriR + pA

DraIII tagggtgatggttcacgtagtgggccatcgccctgatagacggtttttcg 12950

SV40 OriR + pA

DrdI ccctttgacgttggagtccacgttctttaatagtggactcttgttccaaa 13000

SV40 OriR + pA

5' DrdI site

FIG. 6 (Cont'd)

ctggaacaacactcaaccctatctcggtctattcttttgatttataaggg 13050

SV40 OriR + pA attttgccgatttcggcctattggttaaaaaatgagctgatttaacaaaa 13100

SV40 OriR + pA

AclI atttaacgcgaattttaacaaaatattaacgtttacaatttcccaggtgg 13150

SV40 OriR + pA cacttttcggggaaatgtgcgcggaacccctatttgtttatttttctaaa 13200 pBSSK+ plasmid tacattcaaatatgtatccgctcatgagacaataaccctgataaatgctt 13250 pBSSK+ plasmid caataatattgaaaaaggaagagtatgagtattcaacatttccgtgtcgc 13300 pBSSK+ plasmid amp resistance gene ccttattcccttttttgcggcattttgccttcctgtttttgctcacccag 13350 pBSSK+ plasmid amp resistance gene

BssSI aaacgctggtgaaagtaaaagatgctgaagatcagttgggtgcacgagtg 13400 pBSSK+ plasmid amp resistance gene

FIG. 6 (Cont'd)

ggttacatcgaactggatctcaacagcggtaagatccttgagagttttcg 13450 pBSSK+ plasmid amp resistance gene

AclI
XmnI ccccgaagaacgttttccaatgatgagcacttttaaagttctgctatgtg 13500 pBSSK+ plasmid amp resistance gene gcgcggtattatcccgtattgacgccgggcaagagcaactcggtcgccgc 13550 pBSSK+ plasmid amp resistance gene atacactattctcagaatgacttggttgagtACTCACCAGTCACAGAAAA 13600 pBSSK+ plasmid

ScaI...ite amp resistance gene

GCATCTTACGGATGGCATGACAGTAAGAGAATTATGCAGTGCTGCCATAA 13650 amp resistance gene

PvuI

CCATGAGTGATAACACTGCGGCCAACTTACTTCTGACAACGATCGGAGGA 13700 amp resistance gene

CCGAAGGAGCTAACCGCTTTTTTGCACAACATGGGGGATCATGTAACTCG 13750 amp resistance gene

FIG. 6 (Cont'd)

PcsI

CCTTGATCGTTGGGAACCGGAGCTGAATGAAGCCATACCAAACGACGAGC 13800 amp resistance gene

AclI FspI

GTGACACCACGATGCCTGTAGCAATGGCAACAACGTTGCGCAAACTATTA 13850 amp resistance gene

ACTGGCGAACTACTTACTCTAGCTTCCCGGCAACAATTAATAGACTGGAT 13900 amp resistance gene

GGAGGCGGATAAAGTTGCAGGACCACTTCTGCGCTCGGCCCTTCCGGCTG 13950 amp resistance gene

GCTGGTTTATTGCTGATAAATCTGGAGCCGGTGAGCGTGGGTCTCGCGGT 14000 amp resistance gene

ATCATTGCAGCACTGGGGCCAGATGGTAAGCCCTCCCGTATCGTAGTTAT 14050 amp resistance gene

AhdI

CTACACgacggggagtcaggcaactatggatgaacgaaatagacagatcg 14100 amp resistance gene

AhdI Site ctgagataggtgcctcactgattaagcattggtaa 14135 amp resistance gene

FIG. 6 (cont'd)

COMPOSITIONS AND METHODS FOR TREATING ANEMIA

This application is a § 371 application of PCT/US2020/040097, filed Jun. 29, 2020, which claims priority under 35 U.S.C. § 119(e) to U.S. Provisional Patent Application No. 62/868,224, filed Jun. 28, 2019, and U.S. Provisional Patent Application No. 62/910,723, filed Oct. 4, 2019. The foregoing applications are incorporated by reference herein.

FIELD OF THE INVENTION

The present invention relates to the field of hematology. More specifically, the invention provides compositions and methods for the treatment of anemia.

BACKGROUND OF THE INVENTION

Several publications and patent documents are cited throughout the specification in order to describe the state of the art to which this invention pertains. Each of these citations is incorporated herein by reference as though set forth in full.

Sideroblastic anemia occurs due to defects in the heme synthesis pathway. In addition, defects in iron sulfur pathways or other important pathways in the mitochondria of erythroblasts, which indirectly impair heme production, are responsible for the pathogenesis of sideroblastic anemia. A result of these abnormalities is decreased hemoglobin production and abnormal iron metabolism, leading to accumulation of iron in the nucleated immature erythroblasts. These erythroblasts have iron granule loaded mitochondria, which form rings around the nucleus, and are called ring sideroblasts. The exact mechanisms to explain why ring sideroblasts are produced in this type of anemia versus other types of anemia or disorders with iron overload (e.g., thalassemia or hemochromatosis) have not been clarified yet.

Sideroblastic anemia can be congenital or acquired with the latter being more common. There is a spectrum of severity on their effect on patient as well from mild life-long anemia to very severe transfusion-dependent anemia. Various types of sideroblastic anemias differ in terms of underlying mechanisms, symptoms and treatment. The unifying feature to all types is a defect in mitochondrial metabolisms related to iron utilization (Ducamp, et al., Blood (2019) 133(1):59-69; Bergmann, et al., Pediatr. Blood Cancer (2010) 54(2):273-8). Another unifying feature is the ring sideroblasts around the nucleus, which are seen on bone marrow examination with Prussian blue stain and are the hallmark of sideroblastic anemia.

One of the congenital forms of sideroblastic anemia is due to defects in the gene SCL25A38 (Guernsey et al. (2009) Nature Genetics 41(6)651-653; Kannenglessar et al. (2011) Haematologica 96(6):808-813). This is a gene for mitochondrial transporter, likely involved in bringing glycine into mitochondria, which is required for 5-aminolevulinic acid (ALA) production. This type is inherited in an autosomal recessive pattern and is usually a more severe anemia requiring chronic transfusion support.

Currently available therapies for sideroblastic anemia are limited and are largely drawn to only treating symptoms. Thus, there is an ongoing and unmet need for improved compositions and methods for treating anemias such as sideroblastic anemia.

SUMMARY OF THE INVENTION

In accordance with one aspect of the instant invention, nucleic acids and vectors, particularly viral vectors such as lentiviral vectors, are provided. In a particular embodiment, the nucleic acid or vector comprises a nucleic acid molecule comprising any one or more of: i) a 5' long terminal repeat (LTR) and a 3' LTR (e.g., at least one of the LTR may be self-inactivating); ii) at least one polyadenylation signal; iii) at least one promoter; iv) a locus control region (e.g., a globin gene locus control region (LCR)); v) an insulator (e.g., an ankyrin insulator element (Ank)); vi) a Woodchuck Post-Regulatory Element (WPRE) (e.g., wherein the WPRE is 3' of the 3'LTR); vii) enhancer (e.g., beta globin 3' enhancer; operably linked to the nucleic acid encoding the therapeutic protein); viii) a Rev response element (RRE) (e.g., from HIV); and/or ix) a sequence encoding a protein (e.g., a therapeutic protein). The instant invention also encompasses cells (e.g., hematopoietic stem cells, hematopoietic progenitor cells, erythroid progenitor cells, or erythroid cells) and viral particles comprising the nucleic acid or vector (e.g., lentiviral vector) of the instant invention. Compositions comprising the nucleic acid or vector (e.g., lentiviral vector) or viral particles are also encompassed by the instant invention. The compositions may further comprise a pharmaceutically acceptable carrier.

In accordance with another aspect of the instant invention, methods of inhibiting, treating, and/or preventing bone marrow failure (BMF) syndromes (e.g., red blood cell (RBC) specific BMF syndromes) (see, e.g., Wegman-Ostrosky, et al., Br. J. Haematol. (2017) 177(4):526-542), dyserythropoietic syndromes, and/or anemias such as sideroblastic anemia (congenital or acquired sideroblastic anemia) in a subject are provided. In a particular embodiment, the method comprises administering a nucleic acid or viral vector or viral particle of the instant invention to a subject in need thereof. In a particular embodiment, the method comprises an ex vivo therapy utilizing a nucleic acid, viral vector, or viral particle of the instant invention. The nucleic acid, viral vector, or viral particle may be in a composition with a pharmaceutically acceptable carrier.

BRIEF DESCRIPTIONS OF THE DRAWINGS

FIG. 1 provides schematics of an erythroid specific (Ery-SLC25A38) and constitutive (Con-SLC25A38; WPRE optional) lentiviral vectors backbones containing the SLC25A38 gene.

Figure 2:
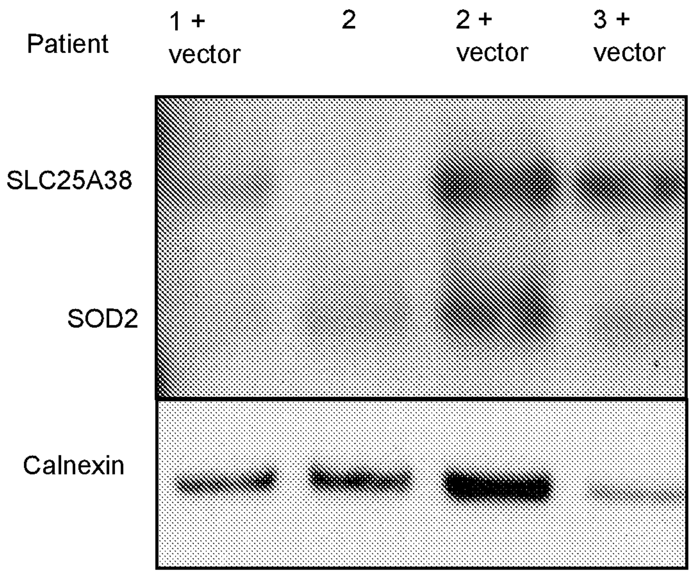

FIG. 2 provides a Western blot of SLC25A38 expression in congenital sideroblastic anemia patient (3 patients) derived hematopoietic progenitor cells either untreated (patient 2) or treated with Con-SLC25A38 (patient 1, 2, or 3+vector). $CD34^+$ cells were harvested from three patients with SLC25A38 mediated congenital sideroblastic anemia (CSA). Transduction of $CD34^+$ progenitor cells with constitutive expressing SLC25A38 vector showed expression of SLC25A38 at the expected protein size compared to no expression in the patient derived cells without vector. Superoxide dismutase 2 (SOD2) and calnexin are provided as controls.

Figure 3:
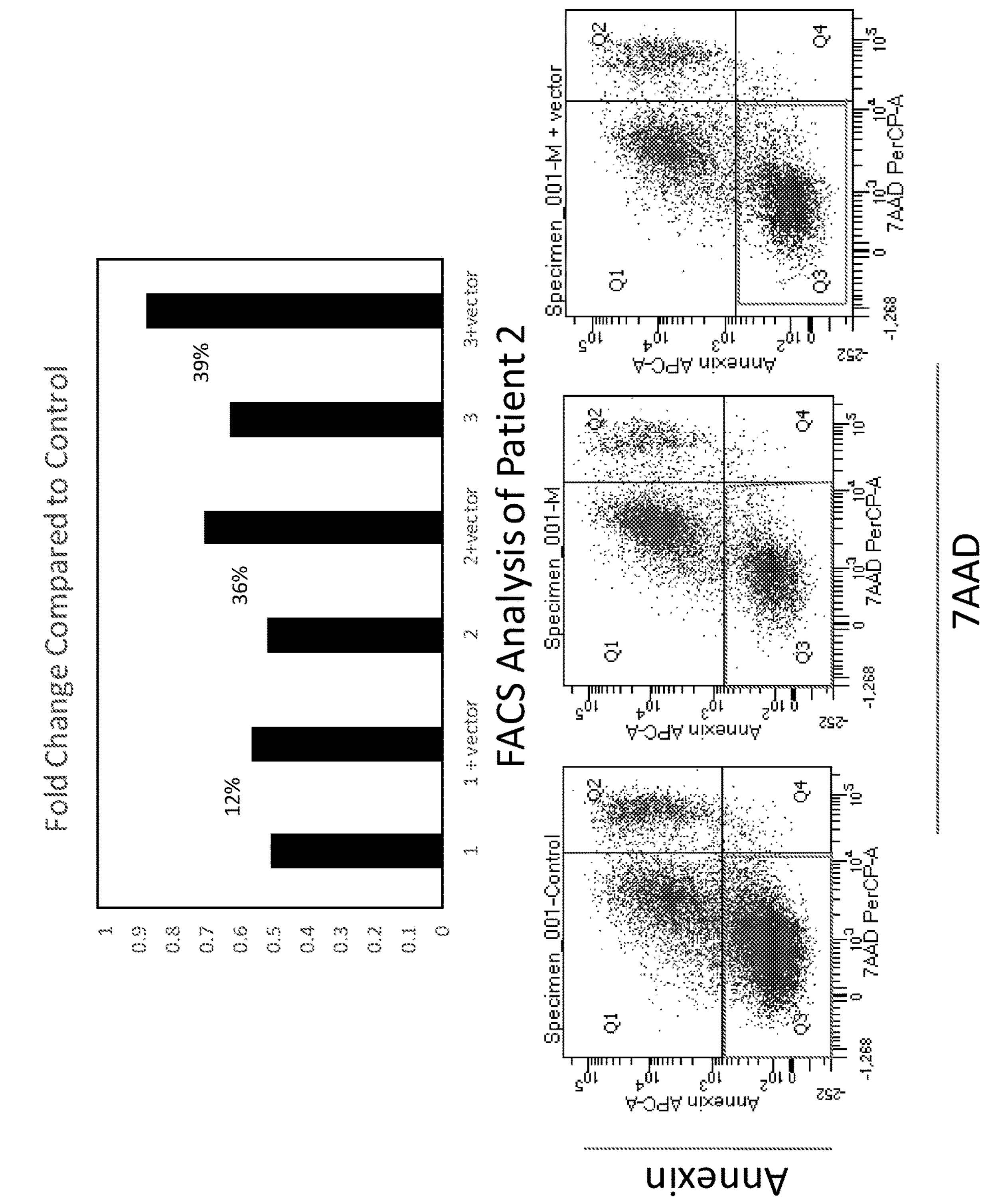

FIG. 3 provides a graph of the fold change in cell viability of congenital sideroblastic anemia patient derived hematopoietic progenitor cells either untreated or treated with Con-SLC25A38 (top). 48 hours after transduction, cells were cultured in erythroid differentiation media for 7 days after which they were analyzed for necrotic and apoptotic cells using Annexin-V and 7-AAD. There was a 12%, 36%, and 39% increase in the number of live cells in the vector transduced cells compared to non-transduced cells with the three patients. FIG. 3 also provides an example of a fluorescence-activated cell sorting (FACS) analysis of cell viability using annexin and 7-aminoactinomycin D (7-AAD) (bottom).

Figure 4:
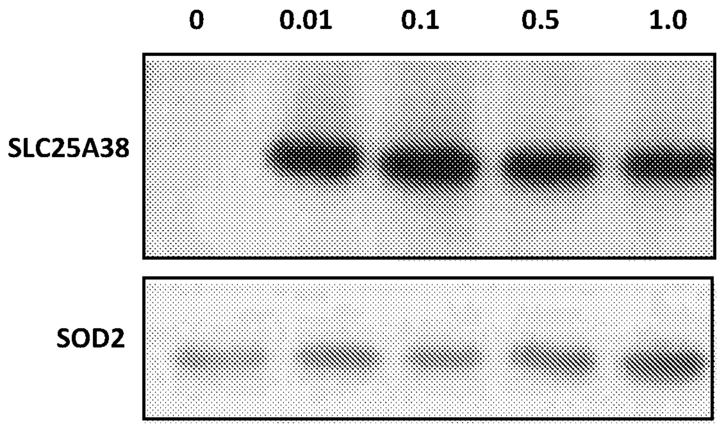

FIG. 4 provides a Western blot of SLC25A38 expression in differentiating murine erythroleukemia (MEL) cells transduced with Ery-SLC25A38. The amount of vector is provided. Superoxide dismutase 2 (SOD2) is provided as a control.

FIG. 5A provides examples of amino acid sequences of human SLC25A38 (SEQ ID NO: 1 (top); SEQ ID NO: 2 (bottom)) and FIG. 5B provides examples of nucleotide sequences encoding human SLC25A38 (SEQ ID NO: 3 (top); SEQ ID NO: 4 (bottom)). FIG. 5C provides an example of an amino acid sequence of human ALAS2 (SEQ ID NO: 5) and FIG. 5D provides an example of a nucleotide sequence encoding human ALAS2 (SEQ ID NO: 6).

Figure 6:
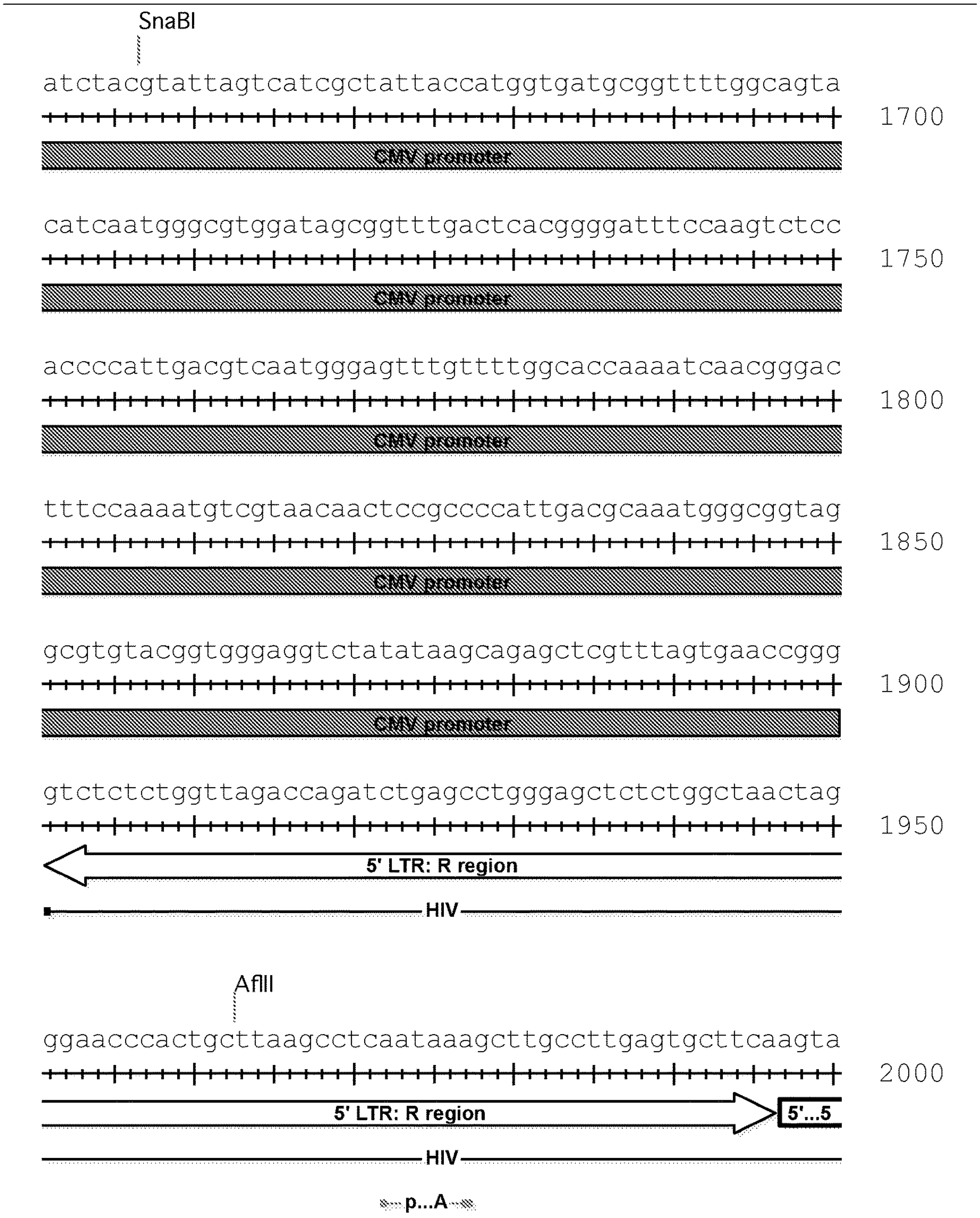
Figure 6:
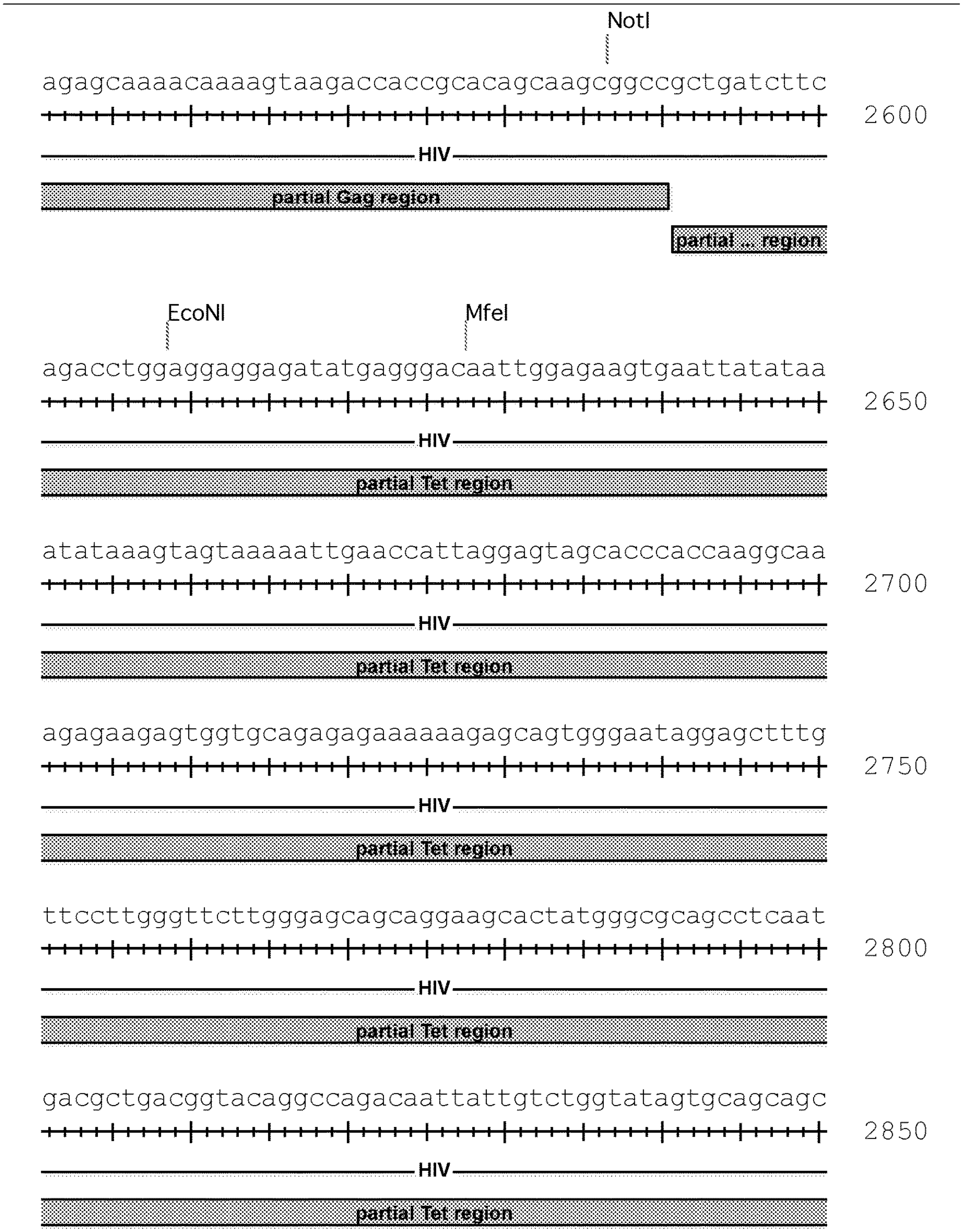
Figure 6:
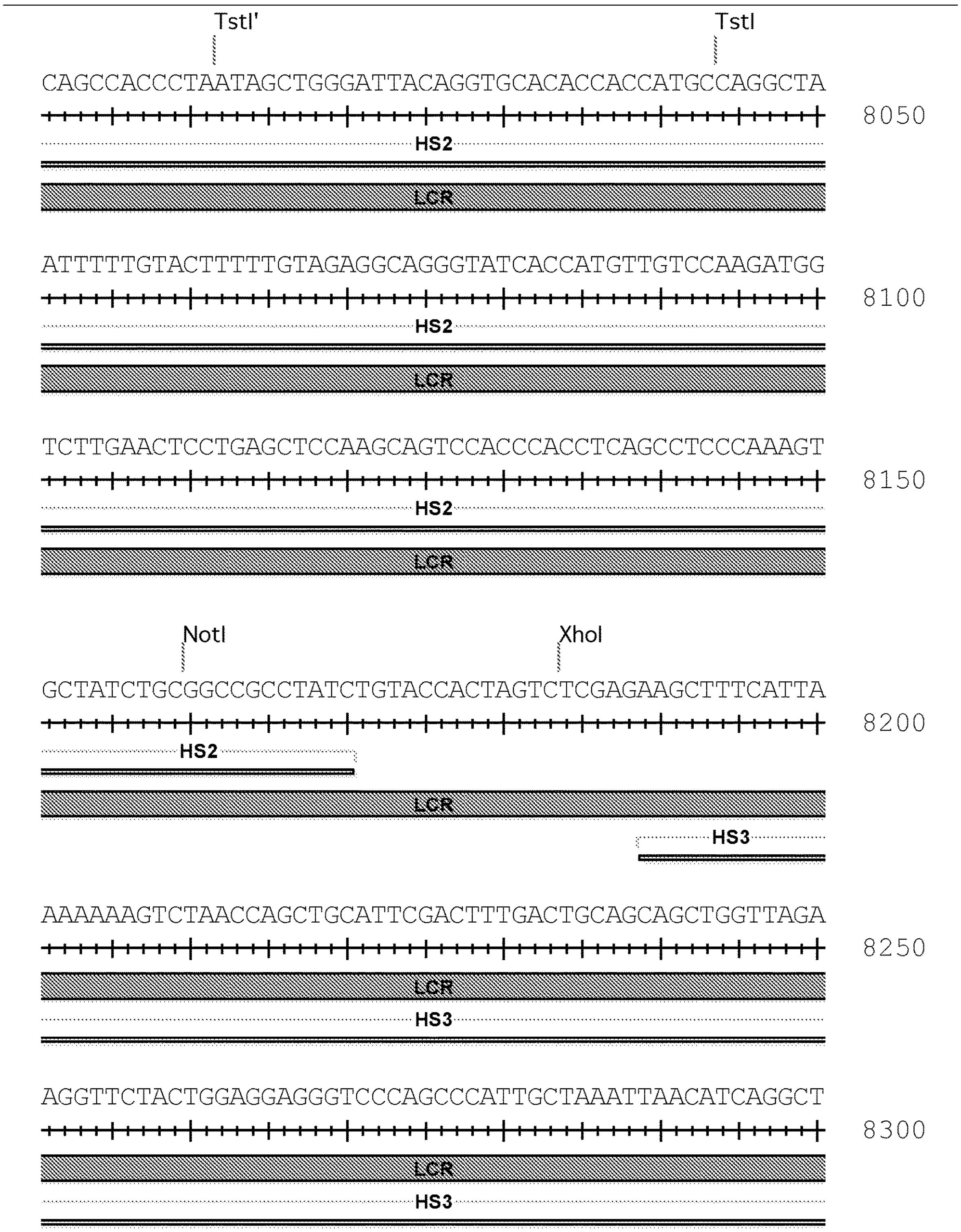
Figure 6:
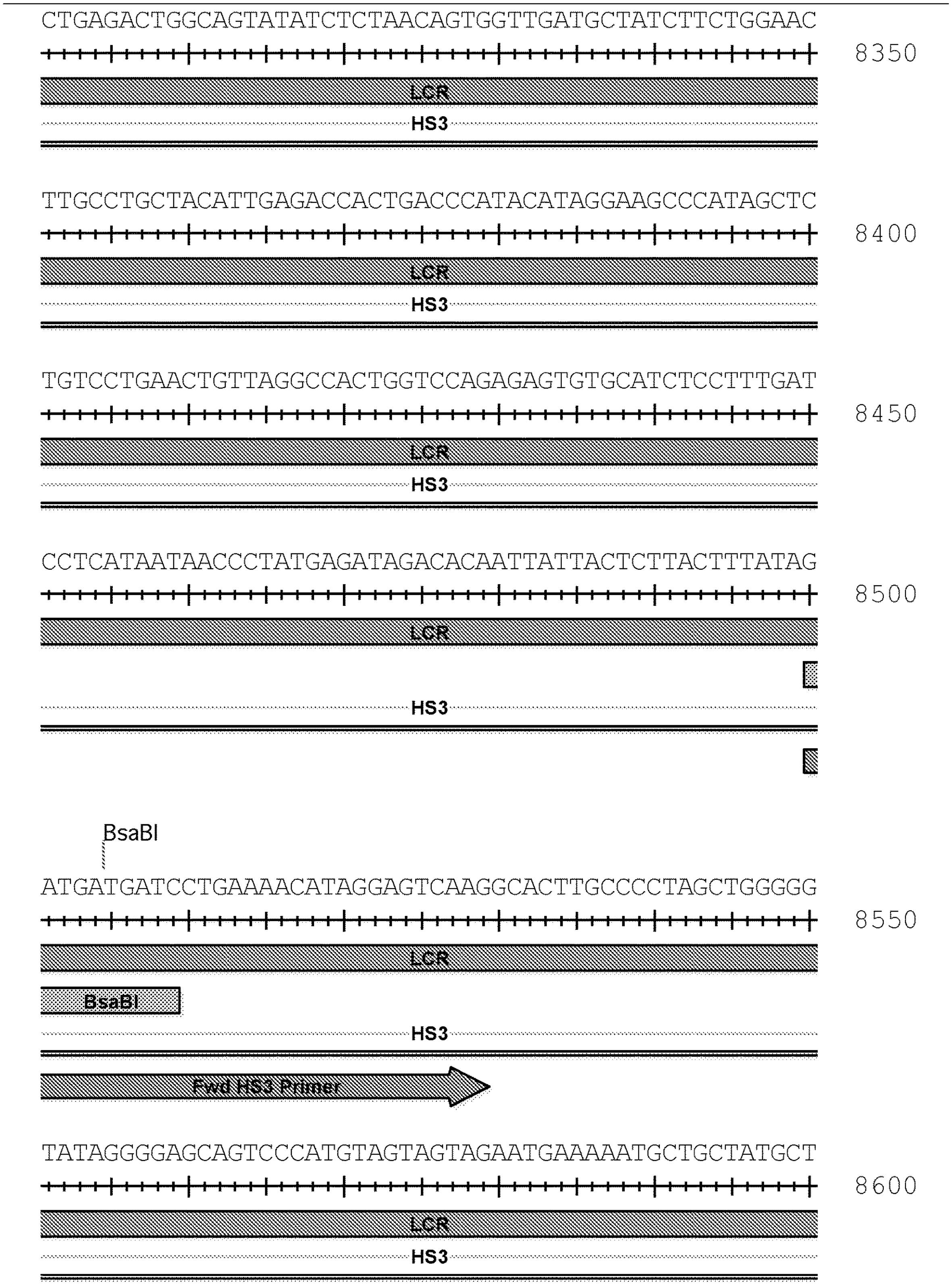
Figure 6:
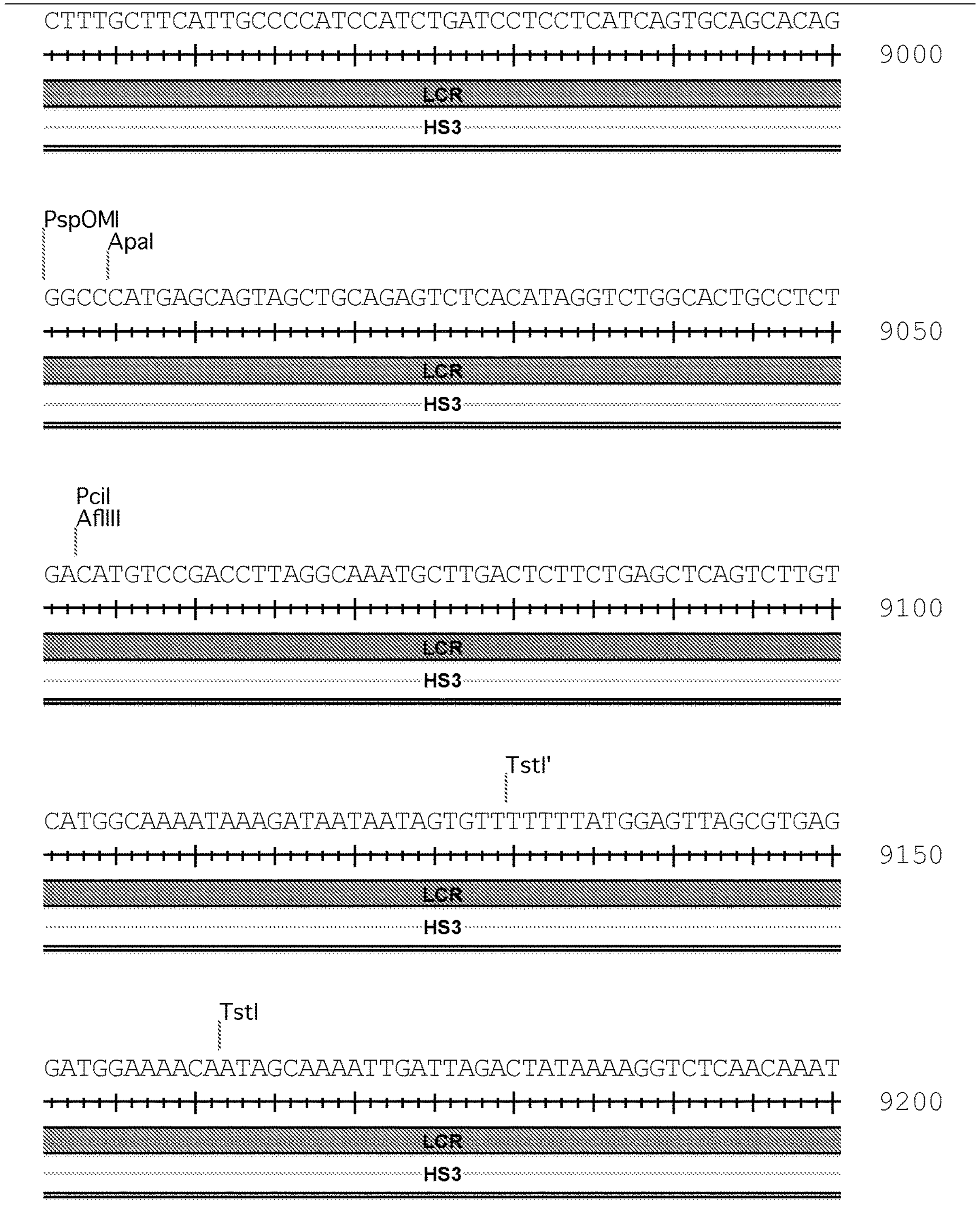
Figure 6:
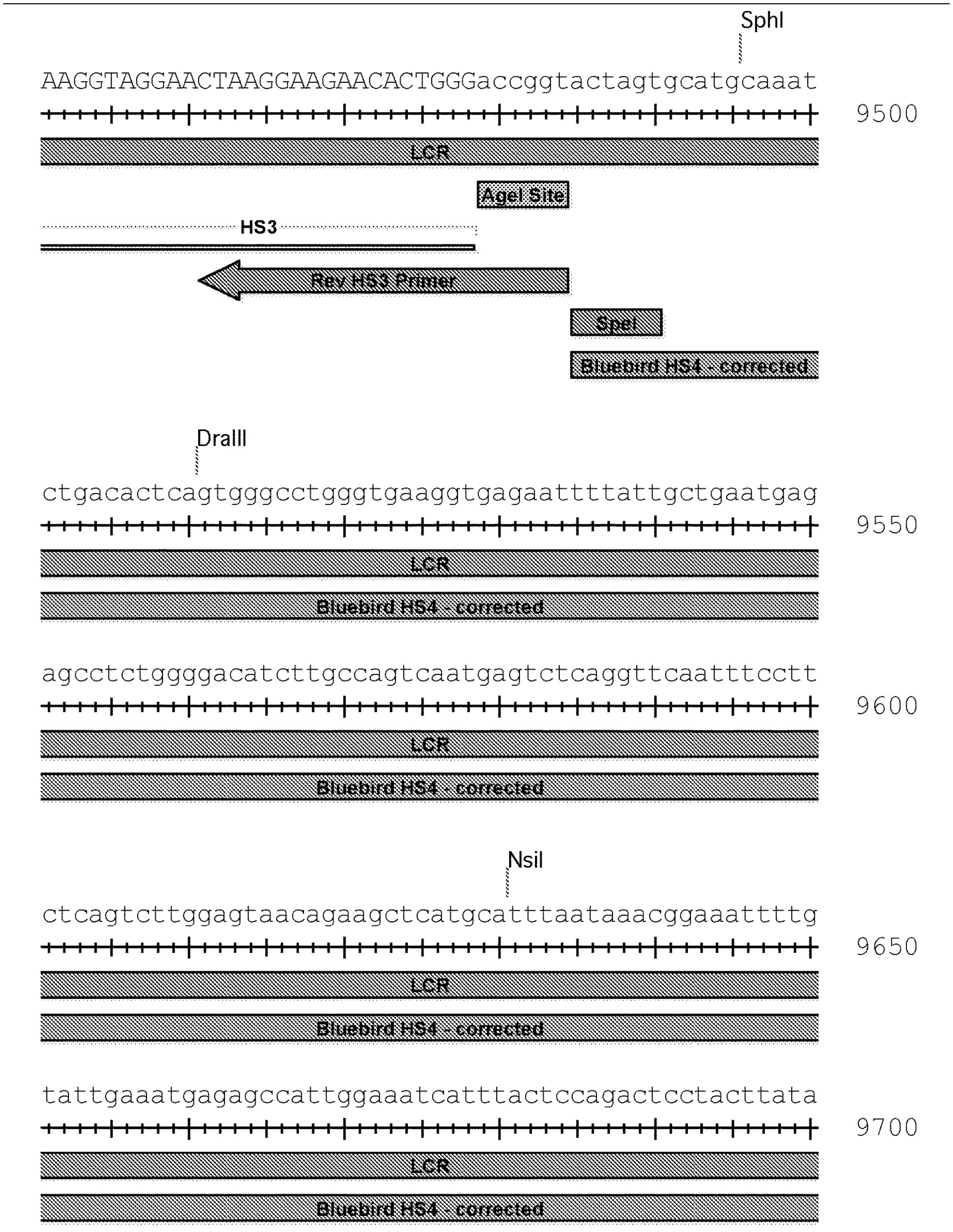
Figure 6:
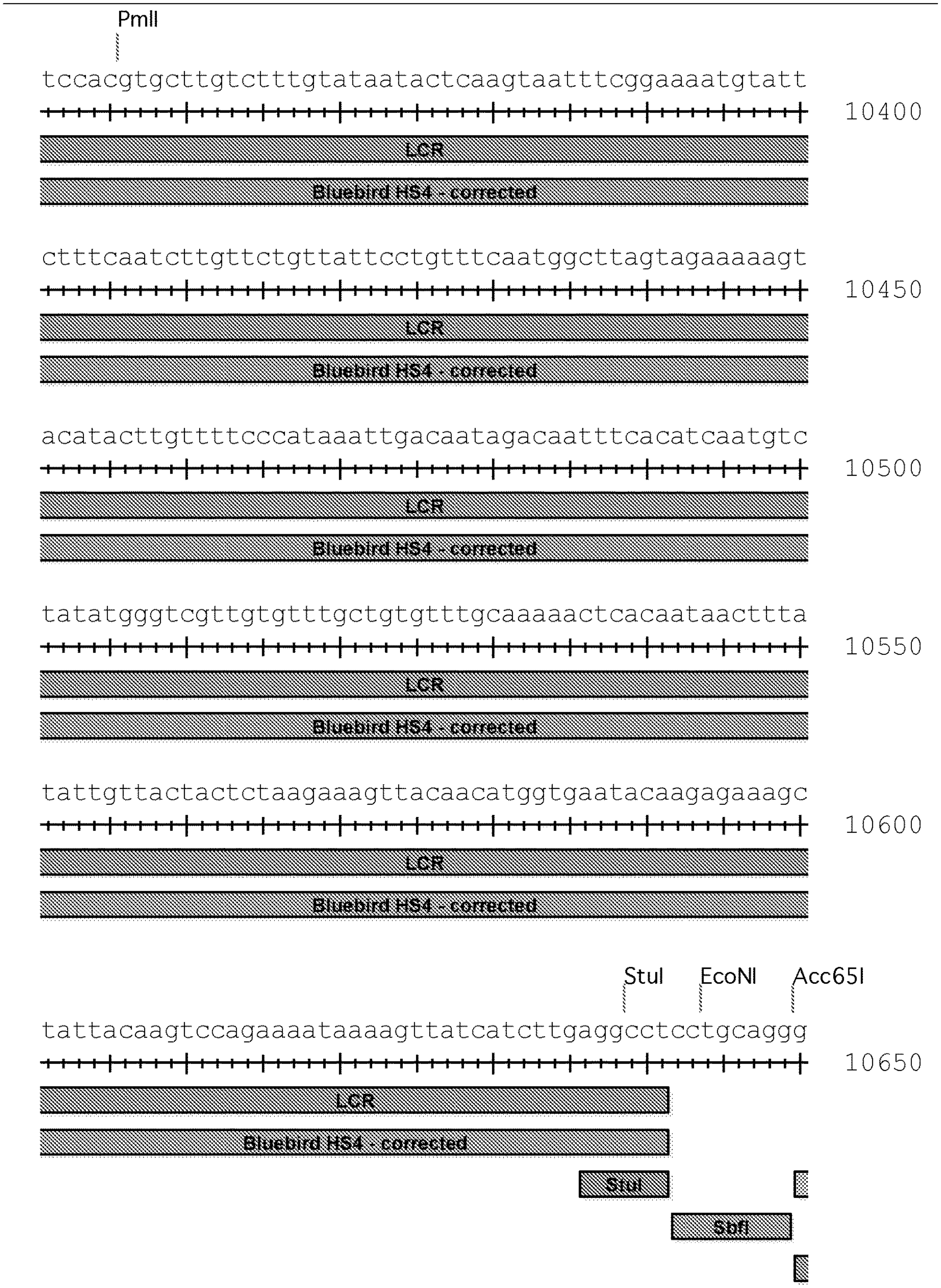
Figure 6:
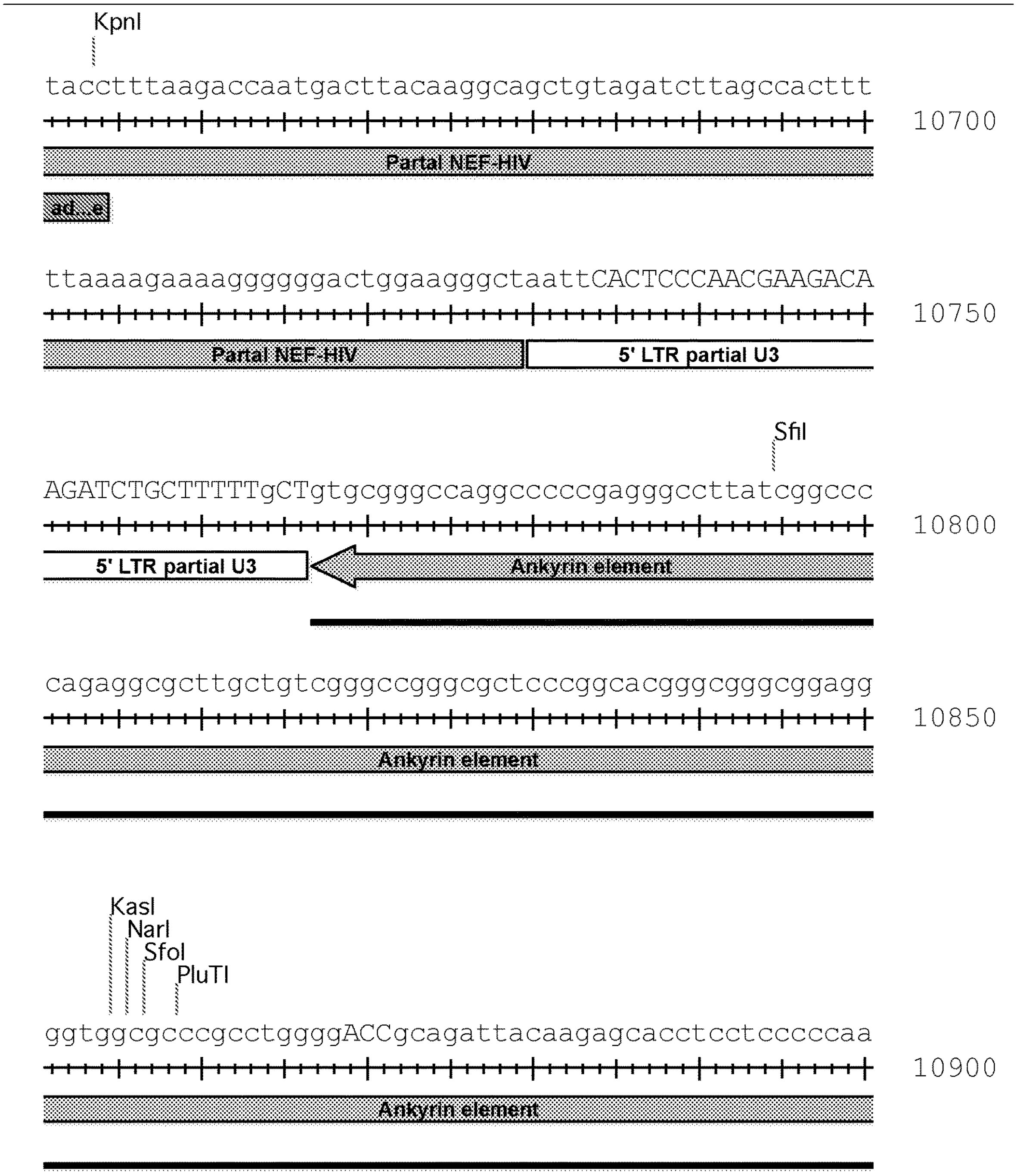
Figure 6:
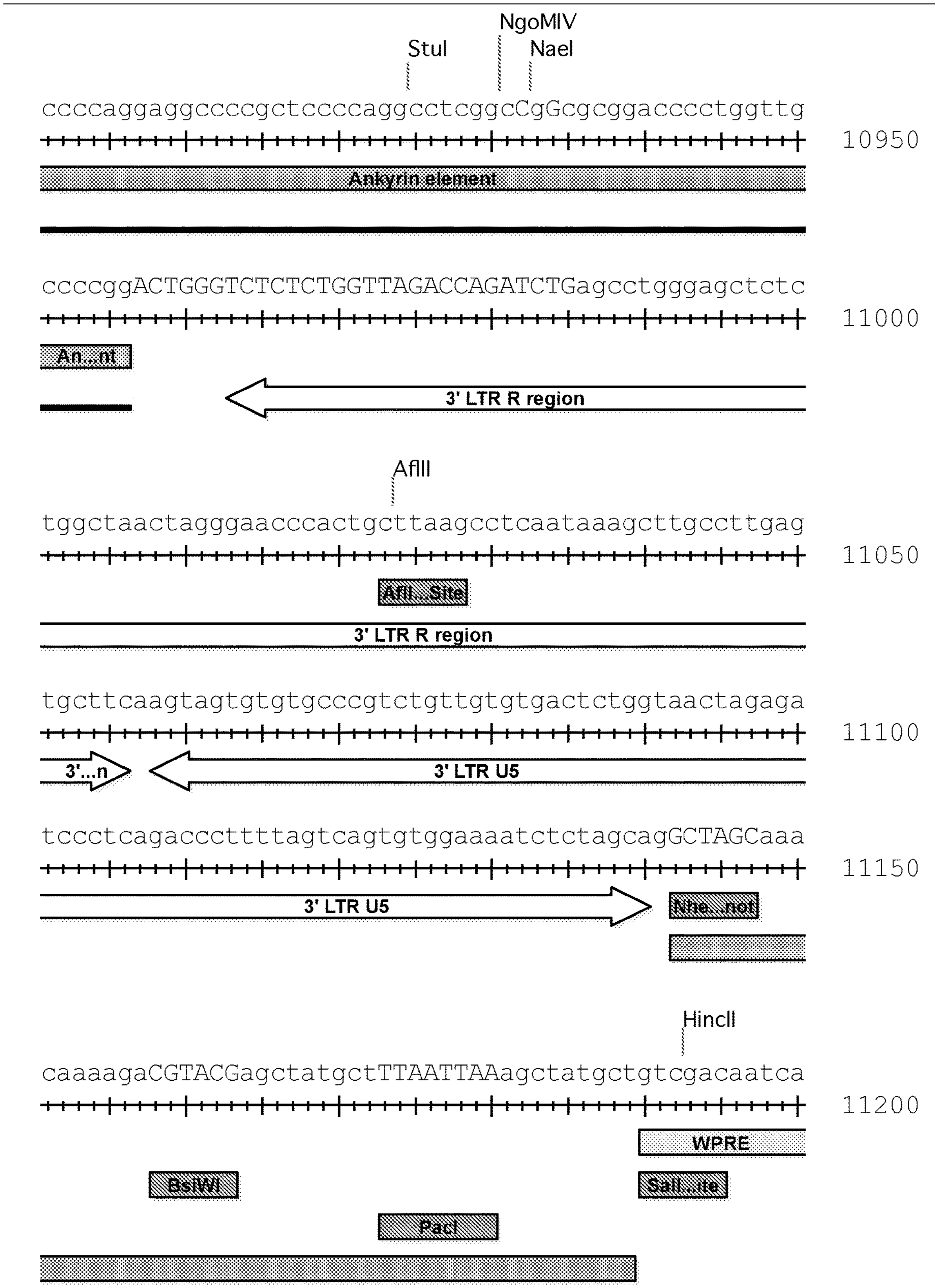
Figure 6:
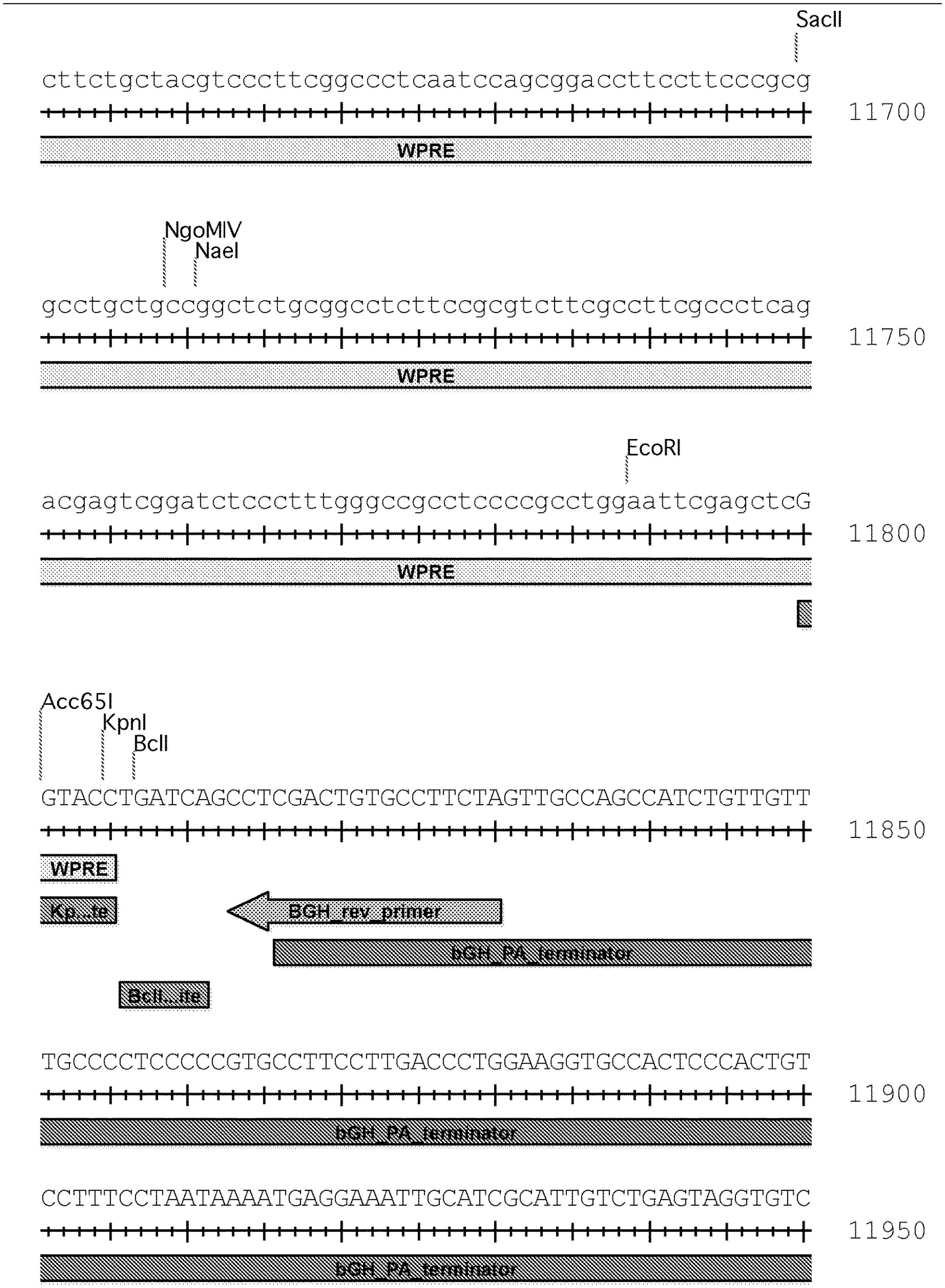

FIG. 6 provides an annotated sequence of ALS17 (SEQ ID NO: 7).

Figure 7A:
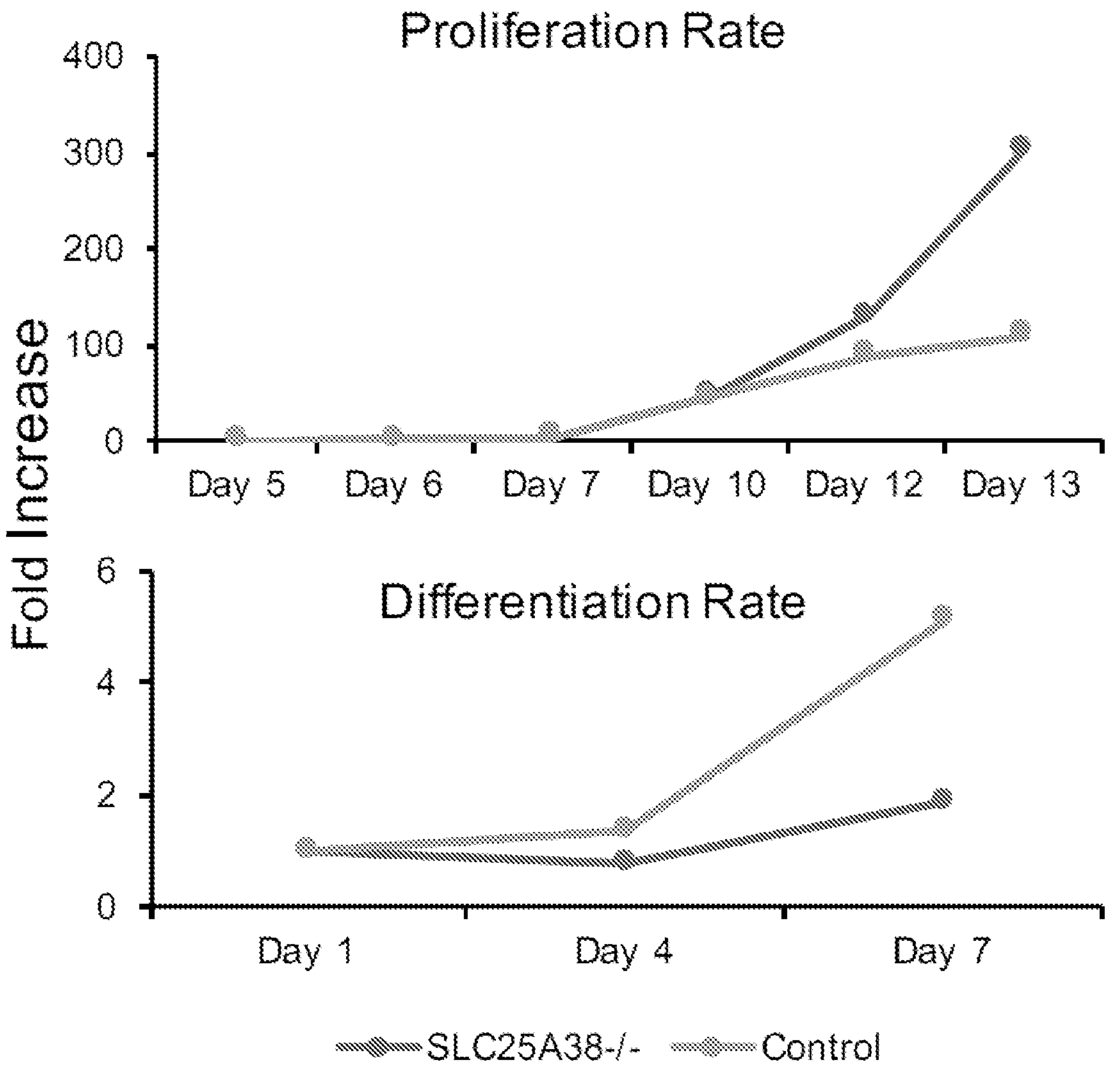
Figure 7B:
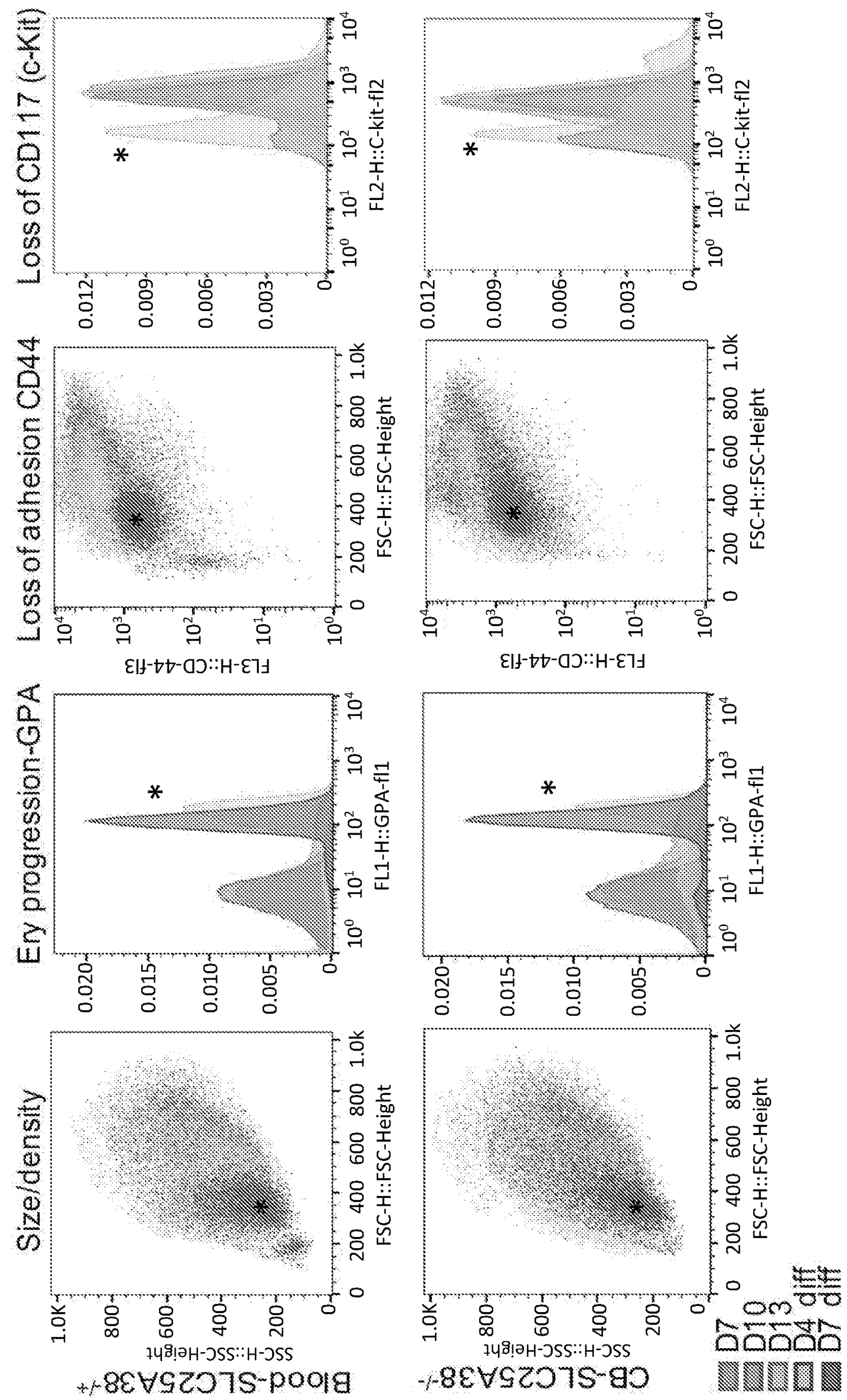
Figure 7C:
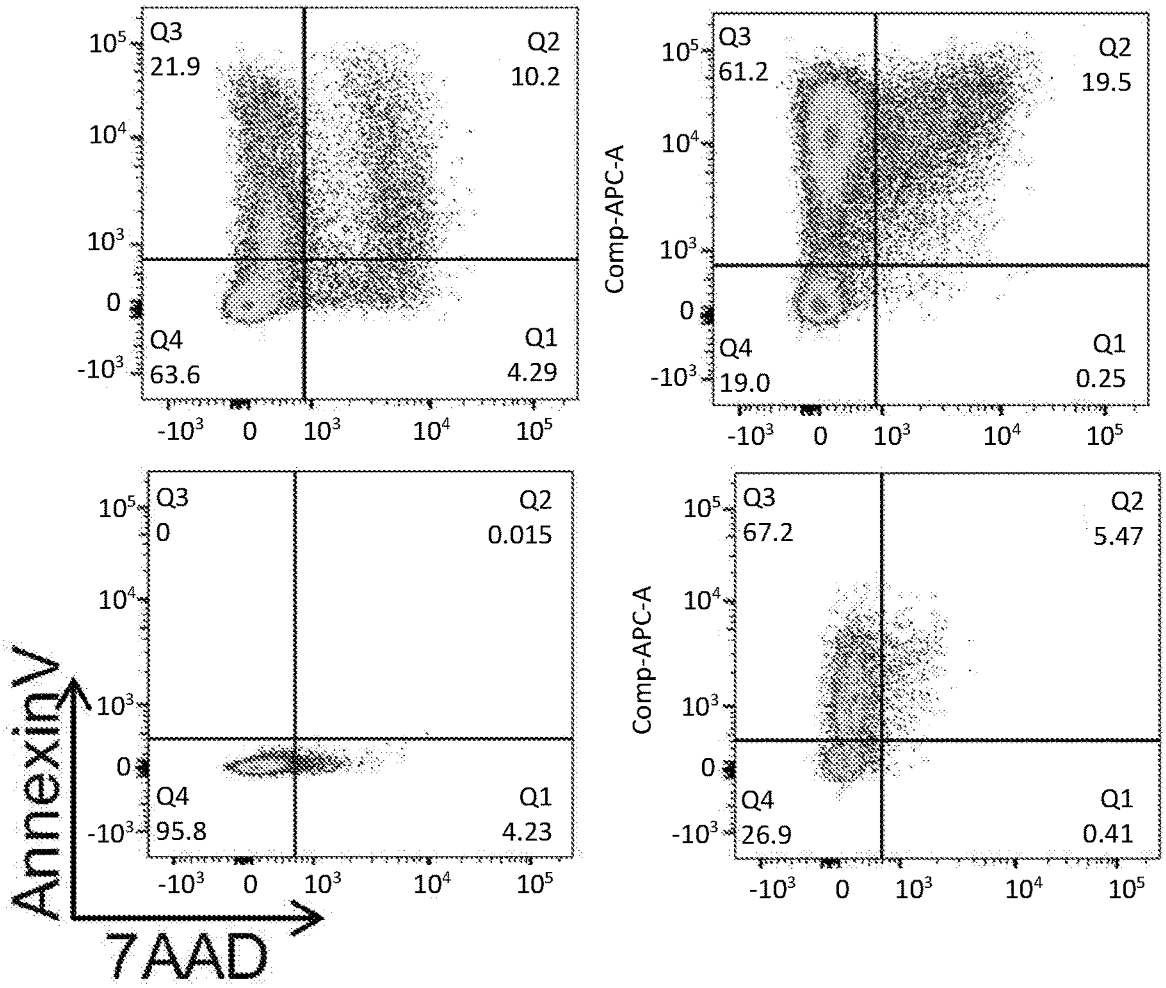
Figure 7D:
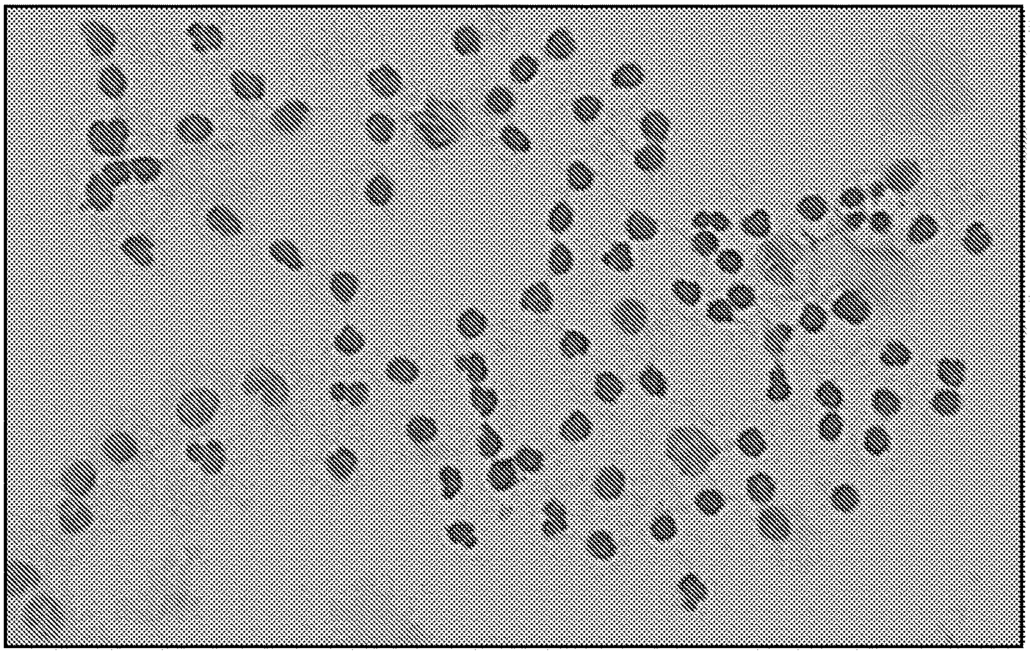

FIG. 7A provides graphs of the proliferation rate (trypan blue assessment, top) and differentiation rate (benzidine staining assessment, bottom) of cord blood-derived $SLC25A38^{-/-}$ hematopoietic progenitor cells (HPCs) versus control $SLC25A38^{-/+}$ HPCs. Cell size reduction, markers of differentiation (GPA) and maintenance of hematopoietic stem cells markers (c-KIT, and adhesion molecule CD44) were followed over time using flow cytometry analyses in $SLC25A38^{-/-}$ and control cells (FIG. 7B). Apoptosis in hemoglobinized $SLC25A38^{-/-}$ and control erythroid cells were measured by annexin5 and 7AAD staining (FIG. 7C). Asterisks identify differentiation peaks. Morphological assessment of $SLC25A38^{-/-}$ erythroid cells on differentiation day 7 showed some iron deposition but not ringed sideroblasts by Prussian blue staining (FIG. 7D).

Figure 8:
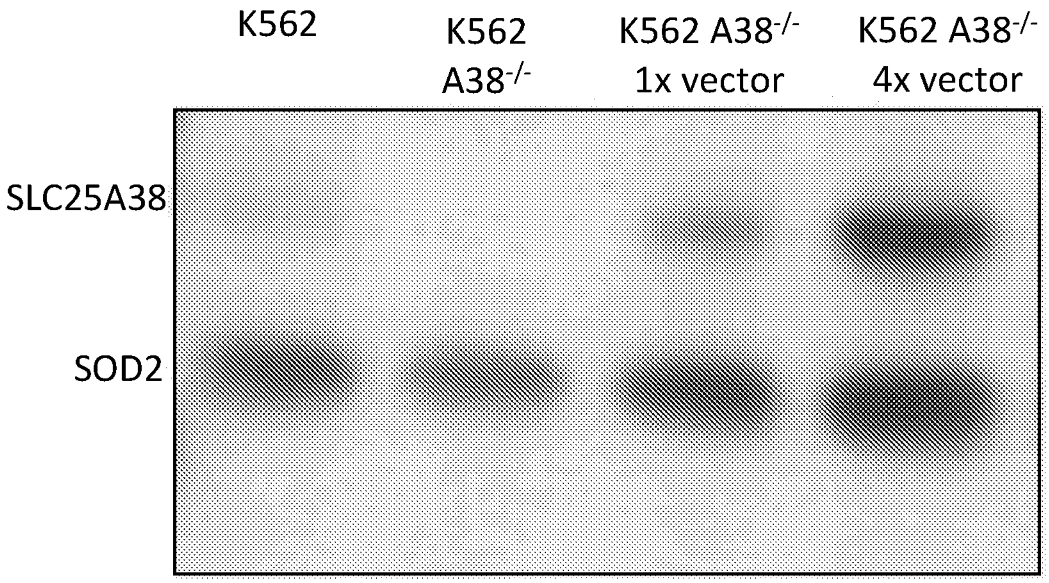

FIG. 8 provides an image of a Western Blot showing SLC25A38 expression in K562 cells, K562 $SLC25A38^{-/-}$ cells, and then a dose dependent expression in K562 $SLC25A38^{-/-}$ cells transduced with 1× or 4× of constitutively expressing SLC25A38 vector. Superoxide dismutase 2 (SOD2) is provided as a control.

Figure 9A:
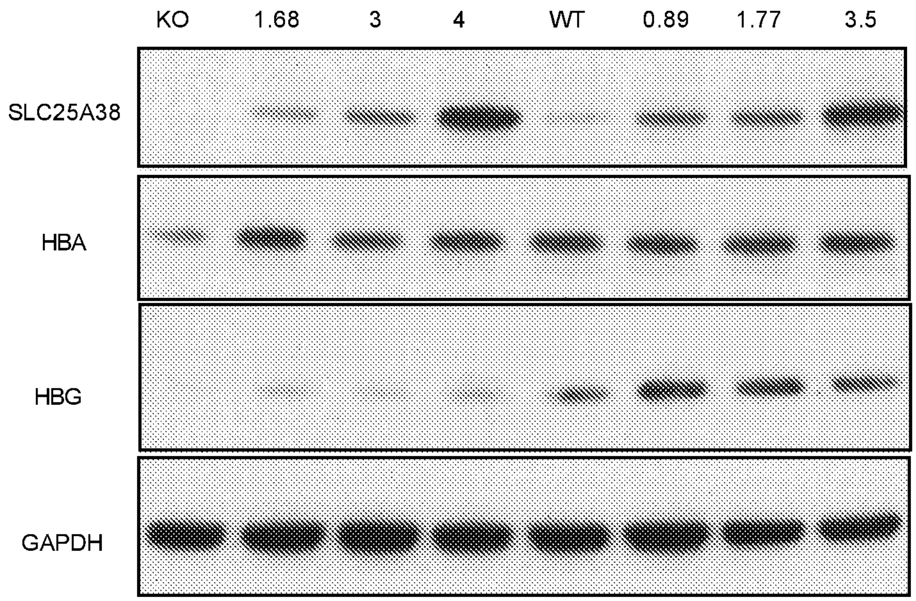
Figure 9B:
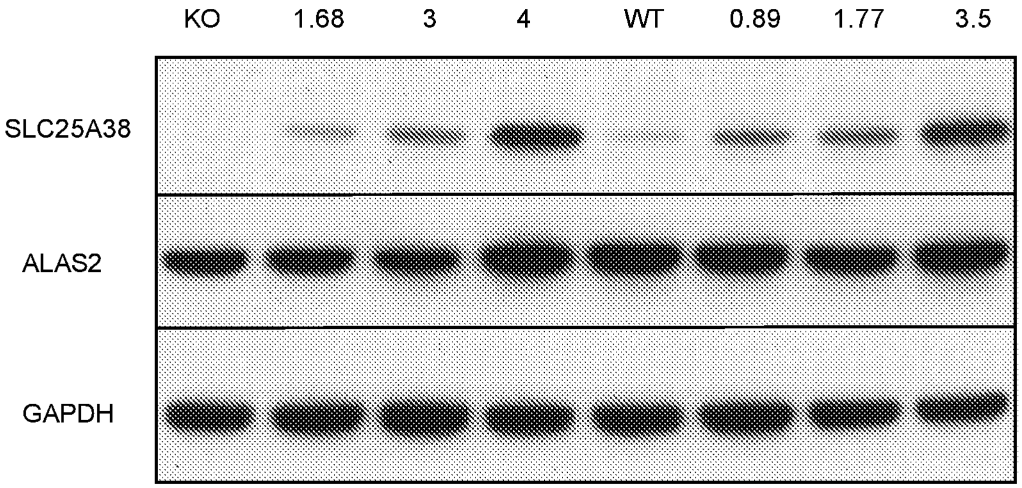
Figure 9C:
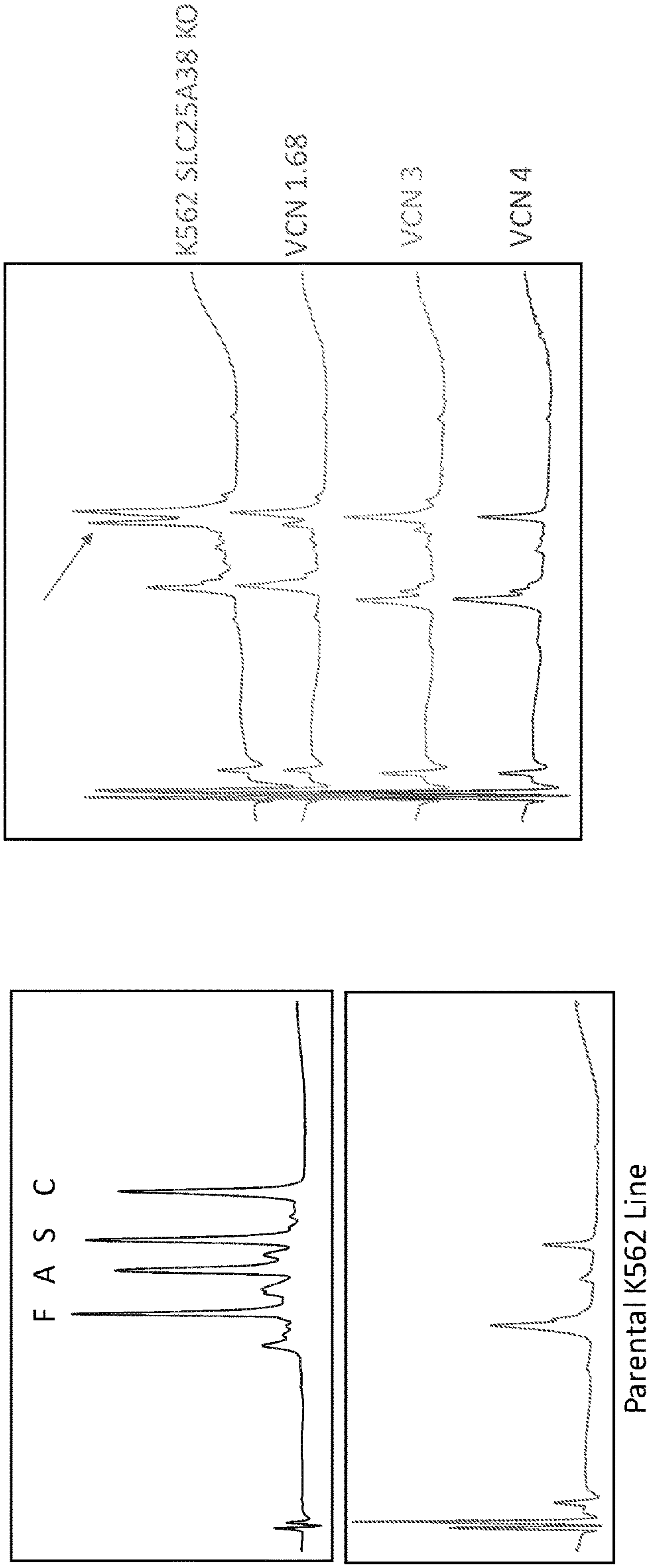
Figure 9D:
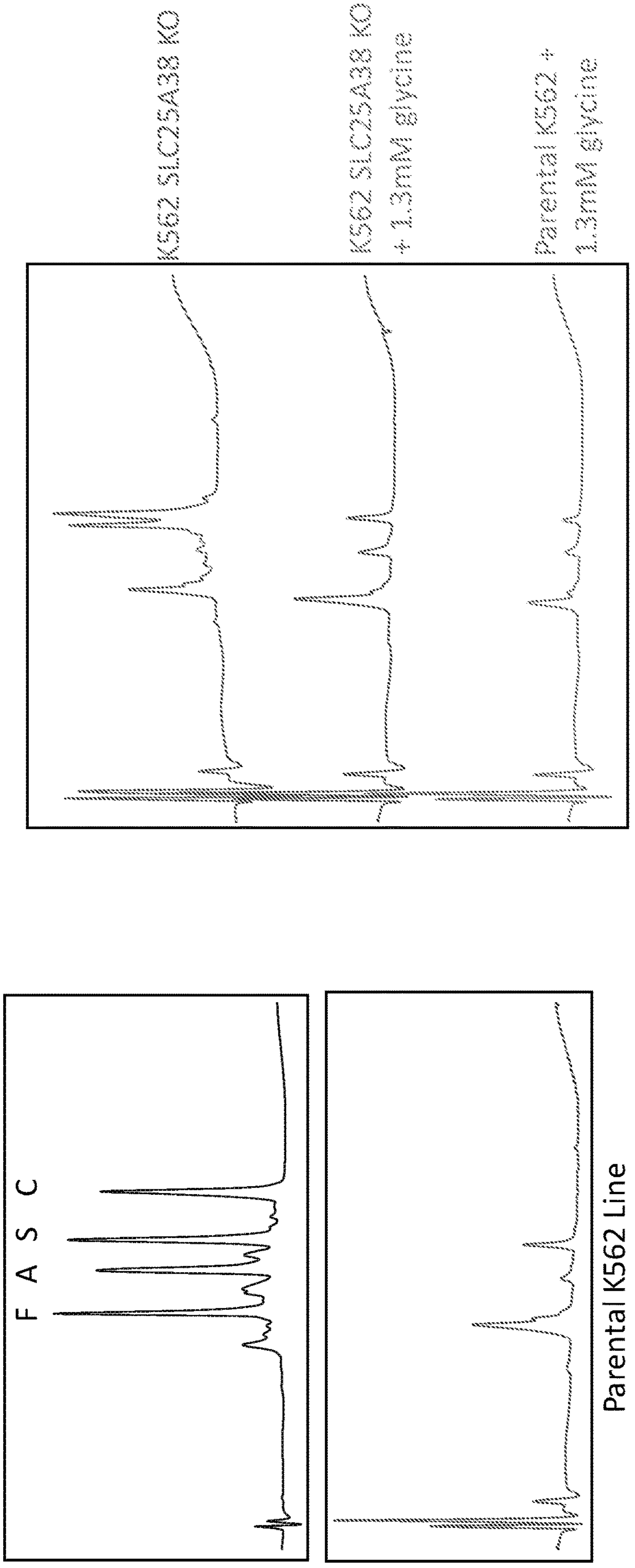

FIG. 9A provides an image of a Western Blot showing SLC25A38, HbA, and HbG expression in K562 cells (right four columns) and K562 $SLC25A38^{-/-}$ cells (left four columns) optionally transduced with the indicated amount of constitutively expressing SLC25A38 vector. Glyceraldehyde 3-phosphate dehydrogenase (GAPDH) is provided as a control. FIG. 9B provides an image of a Western Blot showing SLC25A38, and ALAS2 expression in K562 cells (right four columns) and K562 $SLC25A38^{-/-}$ cells (left four columns) optionally transduced with the indicated amount of constitutively expressing SLC25A38 vector. Glyceraldehyde 3-phosphate dehydrogenase (GAPDH) is provided as a control. FIG. 9C provides reverse phase HPLC graphs of FASC standards (hemoglobin standards containing approximately equal amounts of HbA, HbF, HbS, and HbC; top left), parental K562 cells (bottom left), and K562 $SLC25A38^{-/-}$ cells optionally transduced with the indicated amount of constitutively expressing SLC25A38 vector (right). FIG. 9D provides reverse phase HPLC graphs of FASC standards (top left), parental K562 cells (bottom left), and K562 $SLC25A38^{-/-}$ cells, K562 $SLC25A38^{-/-}$ cells treated with glycine, and parental K562 cells treated with glycine (right).

DETAILED DESCRIPTION OF THE INVENTION

Patients with red blood cell (RBC) specific bone marrow failure (BMF) syndromes represent a particularly difficult cohort to treat. These patients can be transiently maintained on packed red blood cell transfusions but ultimately require curative therapy for which there are very limited options. BMF disorders include, without limitation, acquired aplastic anemia and inherited trilineage aplasia conditions including, for example, Fanconi Anemia and telomere biology disorders; diseases associated with specific failure of red blood cell (RBC) production including, for example, Diamond Blackfan Anemia and congenital sideroblastic anemia; and diseases associated with other single lineage cytopenias including severe congenital neutropenia and inherited thrombocytopenia syndromes (Parikh, et al., Curr. Opin. Pediatr. (2012) 24(1):23-32). While BMF associated with trilineage aplasia can now be cured in greater than 95% of cases by allogeneic stem cell transplantation (alloSCT) using a number of different donor sources and low intensity conditioning, single lineage BMF disorders remain difficult to cure (Peslak, et al., Curr. Treat. Options Oncol. (2017) 18(12):70; Dietz, et al., Curr. Opin. Pediatr. (2016) 28(1): 3-11; Feffault de Latour, et al., Bone Marrow Transplant (2015) 50(9):1168-72; Oved, et al., Biol. Blood Marrow Transplant (2019) 25(3):549-555). RBC-specific BMF diseases are particularly challenging to approach with alloSCT, as chronic RBC transfusion dependence often leads to human leukocyte antigen (HLA) alloimmunization that increases risk of graft failure/rejection with reduced intensity preparative regimens, while transfusional iron overload leads to pre-SCT organ damage that limits the safety of myeloablative alloSCT conditioning approaches (Alter, B. P., Blood (2017) 130(21)2257-2264). Furthermore, many patients with RBC-specific BMF diseases will not have available fully HLA-matched donors for alloSCT, and use of alternative HLA-mismatched donors remains associated with high risk of debilitating graft-versus host disease (Gragert, et al., N. Engl. J. Med. (2014) 371(4):339-48). Additionally, hematopoietic stem cell transplant (HSCT) has offered limited curative potential for patients with CSA (Ayas, et al., Br. J. Haematol. (2001) 113(4):938-9).

In contrast, autologous hematopoietic stem cell (HSC) gene therapy based on lentiviral gene addition, performed with reduced toxicity mono-agent conditioning, is an attractive curative cell therapy approach for RBC-specific BMF diseases, as it eliminates risks of alloimmune complications, and has been associated with tolerable rates of organ toxicity when applied to patients with hemoglobin disorders (Thompson, et al., N. Engl. J. Med. (2018) 378(16):1479-1493). Thus, lentiviral gene correction is a very promising curative modality for these patients. However, the scarcity of each disease in isolation makes this less feasible. Herein, a novel lentiviral vector backbone with an interchangeable transfer gene cassette is provided so that it can be used in multiple RBC specific BMF syndromes.

Specifically, SLC25A38 mediated sideroblastic anemia (particularly congenital sideroblastic anemia (CSA)), an RBC BMF syndrome caused by a defect in heme biosynthesis, was utilized as a proof of principle for the vector. SLC25A38 mediated CSA is the most common autosomal recessive form of the disease. SLC25A38 mutations, which are generally missense or indel changes located in splicing or coding regions, manifest with severe pyridoxine refractory CSA and require chronic RBC transfusions (Kannegiesser, et al., Haematologica (2011) 96(6):808-13). However, the protein is still not well characterized. SLC25A38 is known to provide glycine as a substrate for ALAS2 (5'-aminolevulinate synthase 2 or erythroid ALA-synthase) mediated heme biosynthesis and thus X-linked CSA associated with ALAS2 specific mutations is a target for curative therapy with the optimized vector backbone (Peoc'h et al., Mol. Genet. Metab. (2019) S1096-7192(18)30632-2). Studies in zebrafish and yeast have shown that SLC25A38$^{-/-}$ cells exhibit severely impaired glycine transport (Fernandez-Murray, et al., PLoS Genet. (2016) 12(1):e1005783; LeBlanc, et al., Pediatr. Blood Cancer (2016) 63(7):1307-9; Dufay, et al., G3 (2017) 7(6):1861-1873; Lunetti, et al., J. Biol. Chem. (2016) 291(38):19746-59). However downstream pathophysiologic consequences resulting from this impairment that lead to erythropoietic failure remain poorly defined.

Herein, nucleic acids and viral vectors for the inhibition or treatment of bone marrow failure (BMF) syndromes (e.g., red blood cell (RBC) specific BMF syndromes), dyserythropoietic syndromes, and/or anemias such as sideroblastic anemia (particularly congenital sideroblastic anemia (CSA)) are provided. In a particular embodiment, the viral vector comprises: i) a 5' long terminal repeat (LTR) and a 3' LTR (particularly, at least one of the LTR (at least the 3'LTR) is self-inactivating; a self-inactivating LTR comprises a deletion or mutation relative to its native sequence that results in it being replication incompetent); ii) at least one promoter (e.g., a cell (e.g., erythroid) promoter (e.g., beta-globin promoter (e.g., the 200 bp beta globin promoter)) or a constitutive promoter (e.g., PGK promoter); the promoter may be in antisense orientation); and iii) a sequence encoding a therapeutic protein (optionally a sequence that is a reverse complement to a sequence encoding a therapeutic protein). In a particular embodiment, the promoter is an erythroid promoter. Since SLC25A38 is upregulated during early erythroid differentiation, a lentiviral vector with an erythroid specific promoter can correct the CSA phenotype more efficiently and with less off target effects than a vector with a constitutive promoter. In a particular embodiment, the vector further comprises one or more of: at least one polyadenylation signal (e.g., a strong bovine growth hormone polyA tail (e.g., inserted after the WPRE region) increases lentiviral titers (Zaiss, et al. (2002) J. Virol., 76(14):7209-19)); an enhancer (e.g., a beta globin 3' enhancer; operably linked to the nucleic acid encoding the therapeutic protein); a locus control region (e.g., a globin gene locus control region (LCR)); at least one insulator element (e.g., an ankyrin insulator element (Ank) and/or foamy virus insulator; particularly, the insulator is within the 3' LTR); a Woodchuck Post-Regulatory Element (WPRE) (e.g., configured such that the WPRE does not integrate into a target genome); and/or rev response element (RRE) (particularly, the RRE is from HIV; the RRE may be located between the 5' LTR and the sequence encoding the therapeutic protein). In a particular embodiment, the viral vector comprises: i) a 5' long terminal repeat (LTR) and a self-inactivating 3' LTR; ii) a rev response element (RRE); iii) at least one promoter (e.g., operably linked or controlling expression of the therapeutic protein; optionally in reverse or antisense orientation); iv) a sequence encoding a therapeutic protein (optionally a sequence that is a reverse complement to a sequence encoding a therapeutic protein); v) a globin gene locus control region (LCR); vi) at least one insulator element (e.g., an ankyrin insulator element (Ank) and/or foamy insulator); vii) an enhancer (e.g., operably linked to the nucleic acid encoding the therapeutic protein); and, optionally, at least one polyadenylation signal. In a particular embodiment, the viral vector comprises: i) a 5' long terminal repeat (LTR) and a self-inactivating 3' LTR; ii) a rev response element (RRE); iii) at least one promoter (e.g., operably linked or controlling expression of the therapeutic protein); iv) a sequence encoding a therapeutic protein (optionally a sequence that is a reverse complement to a sequence encoding a therapeutic protein); v) at least one insulator element (e.g., an ankyrin insulator element (Ank) and/or foamy insulator); vi) a Woodchuck Post-Regulatory Element (WPRE); and, optionally, at least one polyadenylation signal. U.S. Patent Application Publication 2018/0008725 and PCT/US2019/029787, both applications are incorporated by reference herein in their entirety, provide viral vectors as well as sequences for certain of the above elements. FIG. 6 provides the sequence of vector ALS17 (SEQ ID NO: 7) which provides an example of nucleotide sequences for certain of the above elements.

In a particular embodiment, the viral vector is Ery-SLC25A38 or Con-SLC25A38 (see, e.g., FIG. 1), optionally wherein the SLC25A38 encoding nucleic acid is replaced with a sequence encoding a different therapeutic protein.

Viral vectors include, for example, retroviruses and lentiviruses. In a particular embodiment, the viral vector is a lentiviral vector. The viral vector may comprise one or more (or all) of the modifications listed below. In a particular embodiment, either Ery-SLC25A38 or Con-SLC25A38 (optionally with a sequence encoding a therapeutic protein other than SLC25A38) comprises one or more (or all) of the modifications listed below.

First, in certain embodiments of the instant invention, the therapeutic protein is SLC25A38 (solute carrier family 25 member 38) or ALAS2 (5'-aminolevulinate synthase 2). In a particular embodiment, the therapeutic protein is human. Examples of amino acid and nucleotide sequences of SLC25A38 are provided in GenBank Gene ID: 54977 and GenBank Accession Nos. NM_001354798.2, NP_001341727.1, NM_017875.4, and NP_060345.2. FIG. 5A provides examples of amino acid sequences of human SLC25A38 and FIG. 5B provides examples of nucleotide sequences encoding human SLC25A38. Examples of amino acid and nucleotide sequences of ALAS2 are provided in GenBank Gene ID: 212 and GenBank Accession Nos. NM_000032.5, NP_000023.2, NM_001037967.4, NP_001033056.1, NM_001037968.4, and NP_001033057.1. In a particular embodiment, the amino acid sequence of human SLC25A38 is SEQ ID NO: 2. In a particular embodiment, the nucleotide sequence encoding human SLC25A38 is SEQ ID NO: 4. In a particular embodiment, the amino acid sequence of SLC25A38 has 80, 81, 82, 83, 84, 85, 86, 87, 88, 89, 90, 91, 92, 93, 94, 95, 96, 97, 98, or 99% identity with SEQ ID NO: 1 or SEQ ID NO: 2. FIG. 5C provides an example of an amino acid sequence of human ALAS2 and FIG. 5D provides an example of a nucleotide sequence encoding human ALAS2. In a particular embodiment, the amino acid sequence of ALAS2 has 80, 81, 82, 83, 84, 85, 86, 87, 88, 89, 90, 91, 92, 93, 94, 95, 96, 97, 98, or 99% identity with SEQ ID NO: 5.

Second, the Woodchuck Post-Regulatory Element, or WPRE can be placed outside the integrating sequence to increase the safety of the vector. An example of a nucleotide sequence of the WPRE is provided in FIG. 6 (e.g., nucleotides 11190-11805). In a particular embodiment, the WPRE is 3' of the 3'LTR. The WPRE increases the titer of the lentivirus, but it can undergo chromosomal rearrangement upon integration. In order to preserve the ability of WPRE to increase viral titers without having this viral element in the integrating sequence, the WPRE can be removed from the integrating portion and added, for example, after the 3'LTR. In addition, a polyadenylation signal (e.g., a bovine growth hormone polyA tail) can be inserted after the WPRE region to increase lentiviral titers (Zaiss, et al. (2002) J. Virol., 76(14):7209-19).

Third, in certain embodiments of the instant invention, the vector may comprise insulators to maximize therapeutic protein expression at a random site of integration and to protect the host genome from possible genotoxicity. Insulators can shelter the transgenic cassette from the silencing effect of non-permissive chromatin sites and, at the same time, protect the genomic environment from the enhancer effect mediated by active regulatory elements (like the LCR) introduced with the vector. The 1.2 Kb cHS4 insulator has been used to rescue the phenotype of thalassemic CD34+ BM-derived cells (Puthenveetil, et al. (2004) Blood, 104 (12):3445-53). Further, fetal hemoglobin can be synthesized in human $CD34^+$-derived cells after treatment with a lentiviral vector encoding the gamma-globin gene, either in association with the 400 bp core of the cHS4 insulator or with a lentiviral vector carrying an shRNA targeting the gamma-globin gene repressor protein BCL 11A (Wilber, et al. (2011) Blood, 117(10):2817-26). The HS2 enhancer of the GATA1 gene has also been used to achieve high beta-globin gene expression in human cells from patients with beta-thalassemia (Miccio, et al. (2011) PLoS One, 6(12): e27955). The use of a 200 bp insulator, derived from the promoter of the ankyrin gene, resulted in a significant amelioration of the thalassemic phenotype in mice and high level of expression was reached in both human thalassemic and SCD cells (Breda, et al. (2012) PloS one 7(3):e32345). An example of a nucleotide sequence of the ankyrin insulator is provided in FIG. 6 (e.g., nucleotides 10956-10768). The foamy virus has a 36-bp insulator located in its long terminal repeat (LTR) which reduces its genotoxic potential (Goodman, et al. (2018) J. Virol., 92:e01639-17).

Fourth, the LCR may be a globin gene locus control region (LCR). In a particular embodiment, the globin gene locus control region is a beta-globin gene locus control region. In a particular embodiment, the LCR comprises at least two, at least three, or all four of HS1, HS2, HS3, and HS4. In a particular embodiment, the LCR comprises HS2 and HS3. In a particular embodiment, the LCR comprises HS2, HS3, and HS4. In a particular embodiment, the LCR comprises HS1, HS2, HS3, and HS4. In a particular embodiment, the LCR is in antisense orientation. In a particular embodiment, only HS2, HS3, and HS4 of the LCR are in antisense orientation. An example of a nucleotide sequence of the LCR is provided in FIG. 6 (e.g., nucleotides 6766-10641). In a particular embodiment, the LCR is operably linked to the promoter of the nucleic acid encoding the therapeutic protein.

Fifth, in certain embodiments of the instant invention, the vector comprises the Rev response element (RRE) from HIV (e.g., located near an LTR). The Rev response element (RRE) of HIV facilitates nucleo-cytoplasmic export of viral mRNAs (Sherpa et al. (2015) Nucleic Acids Res., 43(9): 4676-86; incorporated by reference herein).

In certain embodiment, the nucleic acid or viral vector of the instant invention has a nucleotide sequence identical to those presented herein or they can have least 80, 81, 82, 83, 84, 85, 86, 87, 88, 89, 90, 91, 92, 93, 94, 95, 96, 97, 98, or 99% identity to the nucleotide sequence of a viral vector disclosed herein or to an element of a nucleotide sequence of a viral vector disclosed herein (e.g., the sequences provided in U.S. Patent Application Publication 2018/0008725 and PCT/US2019/029787 or FIG. 5 or 6). In a particular embodiment, the nucleic acid or viral vector of the instant invention comprises the elements of either vector set forth in FIG. 1, particularly in the orientation presented.

The present disclosure provides compositions and methods for the inhibition, prevention, and/or treatment of bone marrow failure (BMF) syndromes (e.g., red blood cell (RBC) specific BMF syndromes), dyserythropoietic syndromes, and/or anemias such as sideroblastic anemia (particularly congenital sideroblastic anemia (CSA)). In particular, the present disclosure provides novel nucleic acids and viral vectors for the inhibition, prevention, and/or treatment of bone marrow failure (BMF) syndromes (e.g., red blood cell (RBC) specific BMF syndromes), dyserythropoietic syndromes, and/or anemias such as sideroblastic anemia (particularly congenital sideroblastic anemia (CSA)). In a particular embodiment, the methods of the instant invention can be used to inhibit, treat, and/or prevent a disease or disorder characterized by a mutant or defective SLC25A38 and/or ALAS2 gene.

In accordance with another aspect of the instant invention, methods of transducing cells with a nucleic acid or viral vector of the instant invention are provided. In a particular embodiment, the transduction is performed with the adjuvant/enhancer LentiBoost™ or cyclosporine H. In a particular embodiment, the viral vector is pseudotyped with Cocal envelope. In a particular embodiment, the transduction is performed by prestimulating for 24 hours and using a 2-hit transduction (e.g., a MOI 10/10 at 16 and 8 hours).

In accordance with the instant invention, compositions and methods are provided for increasing heme and/or hemoglobin production in a cell or subject. The method comprises administering a nucleic acid or viral vector of the instant invention to the cell, particularly a hematopoietic stem cell, erythroid precursor cell or erythroid cell (e.g., CD34+ cell), or subject. In a particular embodiment, the subject has a bone marrow failure (BMF) syndrome (e.g., red blood cell (RBC) specific BMF syndrome), dyserythropoietic syndrome, and/or anemia such as sideroblastic anemia (particularly congenital sideroblastic anemia (CSA)). In a particular embodiment, the subject has congenital sideroblastic anemia (CSA). The viral vector may be administered in a composition further comprising at least one pharmaceutically acceptable carrier.

In accordance with another aspect of the instant invention, compositions and methods for inhibiting (e.g., reducing or slowing), treating, and/or preventing a bone marrow failure (BMF) syndrome (e.g., red blood cell (RBC) specific BMF syndrome), dyserythropoietic syndrome, and/or anemia such as sideroblastic anemia (particularly congenital sideroblastic anemia (CSA)) in a subject are provided. In a particular embodiment, the disease is congenital sideroblastic anemia (CSA). In a particular embodiment, the methods comprise administering to a subject in need thereof a nucleic acid or viral vector of the instant invention. The viral vector may be administered in a composition further comprising at least one pharmaceutically acceptable carrier. The nucleic acid or viral vector may be administered via an ex vivo methods wherein the nucleic acid or viral vector is delivered to a hematopoietic stem cell, erythroid precursor cell or erythroid cell (e.g., CD34+ cell), particularly autologous ones, and then the cells are administered to the subject. In a particular embodiment, the method comprises isolating hematopoietic cells (e.g., erythroid precursor cells) or erythroid cells from a subject, delivering a nucleic acid or viral vector of the instant invention to the cells, and administering the treated cells to the subject. The methods of the instant invention may further comprise monitoring the disease or disorder in the subject after administration of the composition(s) of the instant invention to monitor the efficacy of the method. For example, the subject may be monitored for characteristics of low heme or a bone marrow failure (BMF) syndrome (e.g., red blood cell (RBC) specific BMF syndrome), dyserythropoietic syndrome, and/or anemia such as sideroblastic anemia (particularly congenital sideroblastic anemia (CSA)).

The methods of the instant invention may further comprise the administration of another therapeutic regimen. For example, the methods may further comprise administering glycine, optionally with folate (WO 2014/108812), vitamin B6 (pyridoxine), and or an iron chelating agent (e.g., deferoxamine). In a particular embodiment, the method further comprises giving the subject a blood transfusion.

As explained hereinabove, the compositions of the instant invention are useful for increasing heme and/or hemoglobin production and for treating a bone marrow failure (BMF) syndrome (e.g., red blood cell (RBC) specific BMF syndrome), dyserythropoietic syndrome, and/or anemia such as sideroblastic anemia (particularly congenital sideroblastic anemia (CSA)). A therapeutically effective amount of the composition may be administered to a subject in need thereof. The dosages, methods, and times of administration are readily determinable by persons skilled in the art, given the teachings provided herein.

The components as described herein will generally be administered to a patient as a pharmaceutical preparation. The term "patient" or "subject" as used herein refers to human or animal subjects. The components of the instant invention may be employed therapeutically, under the guidance of a physician for the treatment of the indicated disease or disorder.

The pharmaceutical preparation comprising the components of the invention may be conveniently formulated for administration with an acceptable medium (e.g., pharmaceutically acceptable carrier) such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

The compositions of the present invention can be administered by any suitable route, for example, by injection (e.g., for local (direct) or systemic administration), oral, pulmonary, topical, nasal or other modes of administration. The composition may be administered by any suitable means, including parenteral, intramuscular, intravenous, intraarterial, intraperitoneal, subcutaneous, topical, inhalatory, transdermal, intrapulmonary, intraarterial, intrarectal, intramuscular, and intranasal administration. In a particular embodiment, the composition is administered directly to the blood stream (e.g., intravenously). In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington: The Science and Practice of Pharmacy, 21st edition, Philadelphia, PA. Lippincott Williams & Wilkins. The pharmaceutical composition of the present invention can be prepared, for example, in liquid form, or can be in dried powder form (e.g., lyophilized for later reconstitution).

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the molecules to be administered, its use in the pharmaceutical preparation is contemplated.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous. Injectable suspensions may be prepared, in which case appropriate liquid carriers, suspending agents and the like may be employed. Pharmaceutical preparations for injection are known in the art. If injection is selected as a method for administering the therapy, steps should be taken to ensure that sufficient amounts of the molecules reach their target cells to exert a biological effect.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art. The appropriate dosage unit for the administration of the molecules of the instant invention may be determined by evaluating the toxicity of the molecules in animal models. Various concentrations of pharmaceutical preparations may be administered to mice with transplanted human tumors, and the minimal and maximal dosages may be determined based on the results of significant reduction of tumor size and side effects as a result of the treatment. Appropriate dosage unit may also be determined by assessing the efficacy of the treatment in combination with other standard therapies.

The pharmaceutical preparation comprising the molecules of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

Definitions

The singular forms "a," "an," and "the" include plural referents unless the context clearly dictates otherwise.

The terms "isolated" is not meant to exclude artificial or synthetic mixtures with other compounds or materials, or the presence of impurities that do not interfere with the fundamental activity, and that may be present, for example, due to incomplete purification, or the addition of stabilizers.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers. Suitable pharmaceutical carriers are described in Remington: The Science and Practice of Pharmacy, (Lippincott, Williams and Wilkins); Liberman, et al., Eds., Pharmaceutical Dosage Forms, Marcel Decker, New York, N.Y.; and Rowe, et al., Eds., Handbook of Pharmaceutical Excipients, Pharmaceutical Pr.

The term "treat" as used herein refers to any type of treatment that imparts a benefit to a patient suffering from a disease or disorder, including improvement in the condition of the patient (e.g., in one or more symptoms), delay in the progression of the condition, etc.

As used herein, the term "prevent" refers to the prophylactic treatment of a subject who is at risk of developing a condition and/or sustaining a disease or disorder, resulting in a decrease in the probability that the subject will develop conditions associated with the hemoglobinopathy or thalassemia.

A "therapeutically effective amount" of a compound or a pharmaceutical composition refers to an amount effective to prevent, inhibit, or treat a particular injury and/or the symptoms thereof. For example, "therapeutically effective amount" may refer to an amount sufficient to modulate the pathology associated with a bone marrow failure (BMF) syndromes (e.g., red blood cell (RBC) specific BMF syndromes), dyserythropoietic syndromes, and/or anemias such as sideroblastic anemia (particularly congenital sideroblastic anemia (CSA).

As used herein, the term "subject" refers to an animal, particularly a mammal, particularly a human.

A "vector" is a genetic element, such as a plasmid, cosmid, bacmid, phage or virus, to which another genetic sequence or element (either DNA or RNA) may be attached so as to bring about the replication and/or expression of the attached sequence or element. A vector may be either RNA or DNA and may be single or double stranded. A vector may comprise expression operons or elements such as, without limitation, transcriptional and translational control sequences, such as promoters, enhancers, translational start signals, polyadenylation signals, terminators, and the like, and which facilitate the expression of a polynucleotide or a polypeptide coding sequence in a host cell or organism.

The following example is provided to illustrate various embodiments of the present invention. It is not intended to limit the invention in any way.

EXAMPLE

FIG. 1 provides schematics of Ery-SLC25A38 and Con-SLC25A38. Ery-SLC25A38 is a lentiviral vector that carries the SLC25A38 gene under the regulation of the β-globin promoter and the hypersensitive sites HS2, HS3 of the Locus Control Region (LCR). It also contains an ankyrin insulator to prevent repression of SLC25A38 expression. Con-SLC25A38 is a lentiviral vector that carries the SLC25A38 gene under the regulation of a mild constitutive 3-phosphoglycerate kinase (PGK) promoter. It also included a foamy and ankyrin insulator to assist with protein expression.

The transduction of the Con-SLC25A38 vector (0.5 μl) into human cells led to the constitutive expression of SLC25A38 protein. Specifically, SLC25A38 protein expression was observed in transduced 3T3 and HUDEP-2 cells. Notably, the anti-SLC25A38 antibody from Abcam (Cambridge, United Kingdom) is specific to human SLC25A38 whereas an anti-SLC25A38 antibody from Sigma (St. Louis, MO) recognizes both human and murine protein. As seen in FIG. 2, constitutive SLC25A38 protein expression was observed in congenital sideroblastic anemia patient derived hematopoietic progenitor cells with human-specific anti-SLC25A38 antibody from Abcam. Specifically, cells from 3 patients were treated with virus at 3, 4, or 5 vector copy number (VCN), respectively. Increasing VCN led to greater expression compared to controls.

Con-SLC25A38 also increases cell viability of patient derived cells in a dose dependent manner. As seen in FIG. 3, Con-SLC25A38 transduced congenital sideroblastic anemia patient derived hematopoietic progenitor cells have increased viability during erythroid differentiation in a dose dependent manner.

In addition to the above, it was determined that Ery-SLC25A38 expresses SLC25A38 in differentiating murine erythroleukemia (MEL) cells (FIG. 4). Cells were transduced with virus and incubated for 48 hours. They were then induced to differentiate with hexamethylene bisacetamide (HMBA) and 5 days later cell lysates were collected for Western blot analysis.

SLC25A38 mediated CSA causes transfusion dependent anemia due to a defect in erythrocyte differentiation. SLC25A38 has not been well characterized in humans, though its expression has been shown to be increased in erythrocytes. Using established protocols, $CD34^+$ hematopoietic stem cells were isolated from healthy donors, patients heterozygous for loss-of-function SLC25A38 mutations and patients with severe homozygous SLC25A38 457-1G>T CSA. Cells were cultured and maintained in an undifferentiated state to proliferate for 14 days in glycine containing media. They were then transferred to erythroid differentiation media for 7 days. During the proliferative state in which media is supplemented with human serum, plasma, transferrin, IL3, and human stem cell factor (hSCF), the cells from patients with CSA divided at the same rate as control cells (derived from a family member heterozygous for the 457-1G>T mutation), and even surpassed the proliferation rate of control cells at day 13 (FIG. 7A, top). These cells, however, had a significantly slower proliferation rate (0.37× compared to control cells) when cultured in erythroid differentiation media. Benzidine staining showed decreased hemoglobinized cells in CSA versus control-derived cell cultures, indicating that SLC25A38 function is critical to enable completion of erythroid differentiation (FIG. 7A, bottom). A flow cytometry analysis was used to analyze erythroid surface markers taken at 3 time points during proliferation and 2 time points during differentiation. Compared with control cells, the SLC25A38-mutant $CD34^+$ cells exhibited lower expression of glycophorin A (GPA) and retained higher expression of CD117 (c-KIT) out to day 7 in differentiation media, indicating less efficient erythroid differentiation (FIG. 7B).

Using reverse-phase High Performance Liquid Chromatography (HPLC) and spectrophotometry on the hemolysate from $0.5\times10^{6}$ benzidine positive SLC25A38-mutant erythroid cells, 50% of the hemoglobin content was observed in the hemolysate of CSA-derived cells compared to that seen in an equal number of control erythroid cells. Hemoglobinized CSA cells had a significantly higher rate of apoptosis (80%) compared to controls (30%) (FIG. 7C). CSA-derived cells also exhibited iron deposition when stained with Prussian Blue (FIG. 7D). Taken together, these data indicate that the SLC25A38 channel is necessary in late stages of erythroid differentiation and establish robust culture conditions.

In order to create a more versatile and rapid in vitro system for experiments aimed at characterizing and also correcting the CSA phenotype, K562 cells are being utilized, which are a myeloid leukemia cell line with the ability to differentiate to erythrocytes when stimulated with sodium butyrate. Three unique $SLC25A38^{-/-}$ K562 clones have been generated with CRISPR/Cas9. These clones are unable to differentiate into erythrocytes or produce functional hemoglobin when exposed to sodium butyrate thus making them an ideal and versatile system for vector optimization. K562 SLC25A38 knockout (KO) cells can be partially rescued by glycine (1.3 mM). These cells have been transduced with the vectors of the instant invention and protein expression has been observed (FIG. 8).

SLC25A38 addition was also found to correct HbA but not HbG production in K562 KO cells (FIG. 9A). Notably, SLC25A38 expression does not significantly alter ALAS2 expression (FIG. 9B). Reverse-phase High Performance Liquid Chromatography (HPLC) was used to analyze the hemoglobin in SLC25A38 K562 knockout cells. As seen in FIG. 9C, SLC25A38 K562 knockout cells have an additional tetramer that is corrected with SLC25A38 gene addition. Supratherapeutic glycine was also found to correct the SLC25A38 KO tetramer changes (FIG. 9D).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A lentiviral vector comprising a nucleic acid molecule comprising:

i) a 5' long terminal repeat (LTR) and a 3' LTR, wherein at least one of said LTR is self-inactivating;

ii) an beta globin promoter;

iii) an ankyrin insulator element within the 3' LTR;

iv) a sequence encoding a therapeutic protein, wherein said therapeutic protein is solute carrier family 25 member 38 (SLC25A38) or 5'-aminolevulinate synthase 2 (ALAS2);

v) the Dnase I hypersensitive site 2 (HS2) and the HS3 from a human beta globin gene locus control region operably linked to the beta globin promoter; and vi) a human beta globin 3' enhancer operably linked to the sequence encoding the therapeutic protein.

2. The lentiviral vector of claim 1, further comprising a polyadenylation signal.

3. The lentiviral vector of claim 1, further comprising a Woodchuck Post-Regulatory Element (WPRE).

4. The lentiviral vector of claim 1, further comprising a Rev response element (RRE).

5. The lentiviral vector of claim 1, wherein said therapeutic protein is ALAS2.

6. Isolated CD34+ cells comprising the lentiviral vector of claim 1.

7. The lentiviral vector of claim 1, further comprising a Rev response element (RRE) and Woodchuck Post-Regulatory Element (WPRE).

8. A composition comprising the lentiviral vector of claim 1 and a pharmaceutically acceptable carrier.

9. A composition comprising viral particles, wherein the viral particles comprise the lentiviral vector of claim 1.

10. A method of inhibiting and/or treating anemia in a subject having X-linked sideroblastic anemia, said method comprising introducing the lentiviral vector into hematopoietic stem cells or erythrocyte progenitor cells and intravenously administering the hematopoietic stem cells or erythrocyte progenitor cells to the subject, wherein said lentiviral vector comprises a nucleic acid molecule comprising:

i) a 5' long terminal repeat (LTR) and a 3' LTR, wherein at least one of said LTR is self-inactivating;

ii) a beta globin promoter;

iii) an ankyrin insulator element within the 3' LTR;

iv) a sequence encoding a therapeutic protein, wherein said therapeutic protein is 5'-aminolevulinate synthase 2 (ALAS2);

v) the Dnase I hypersensitive site 2 (HS2) and the HS3 from a human beta globin gene locus control region operably linked to the beta globin promoter; and vi) a human beta globin 3' enhancer operably linked to the sequence encoding the therapeutic protein, wherein the hematopoietic stem cells or erythrocyte progenitor cells are isolated from the subject to be treated.

11. The isolated CD34+ cells of claim 6, wherein the CD34+ cells have been isolated from an individual who has sideroblastic anemia.

12. The lentiviral vector of claim 1, wherein the lentiviral vector lacks HS1 and HS4 from the beta globin gene locus control region.

13. The method of claim 10, wherein the lentiviral vector lacks HS1 and HS4 from the beta globin gene locus control region.

* * * * *

SEQUENCE LISTING

```
<160> NUMBER OF SEQ ID NOS: 7

<210> SEQ ID NO 1
<211> LENGTH: 237
<212> TYPE: PRT
<213> ORGANISM: Homo sapiens

<400> SEQUENCE: 1

Met Ile Gln Asn Ser Arg Pro Ser Leu Leu Gln Pro Gln Asp Val Gly
1               5                   10                  15

Asp Thr Val Glu Thr Leu Met Leu His Pro Val Ile Lys Ala Phe Leu
            20                  25                  30

Cys Gly Ser Ile Ser Gly Thr Cys Ser Thr Leu Leu Phe Gln Pro Leu
        35                  40                  45

Asp Leu Leu Lys Thr Arg Leu Gln Thr Leu Gln Pro Ser Asp His Gly
    50                  55                  60

Ser Arg Arg Val Gly Met Leu Ala Val Leu Leu Lys Val Val Arg Thr
65                  70                  75                  80

Glu Ser Leu Leu Gly Leu Trp Lys Gly Met Ser Pro Ser Ile Val Arg
                85                  90                  95

Cys Val Pro Gly Val Gly Ile Tyr Phe Gly Thr Leu Tyr Ser Leu Lys
            100                 105                 110

Gln Tyr Phe Leu Arg Gly His Pro Pro Thr Ala Leu Glu Ser Val Met
        115                 120                 125

Leu Gly Val Gly Ser Arg Ser Val Ala Gly Val Cys Met Ser Pro Ile
    130                 135                 140

Thr Val Ile Lys Thr Arg Tyr Glu Ser Gly Lys Tyr Gly Tyr Glu Ser
145                 150                 155                 160

Ile Tyr Ala Ala Leu Arg Ser Ile Tyr His Ser Glu Gly His Arg Gly
                165                 170                 175

Leu Phe Ser Gly Leu Thr Ala Thr Leu Leu Arg Asp Ala Pro Phe Ser
            180                 185                 190

Gly Ile Tyr Leu Met Phe Tyr Asn Gln Thr Lys Asn Ile Val Pro His
        195                 200                 205

Gly Leu Trp Thr Thr Trp Leu Leu Pro Arg Trp His Pro Pro Ser Pro
```

```
    210                 215                 220

Pro Gln Asn Ser Asn Gly Ser Asn Gly Val Asp Gly Val
225                 230                 235


<210> SEQ ID NO 2
<211> LENGTH: 304
<212> TYPE: PRT
<213> ORGANISM: Homo sapiens

<400> SEQUENCE: 2

Met Ile Gln Asn Ser Arg Pro Ser Leu Leu Gln Pro Gln Asp Val Gly
1               5                   10                  15

Asp Thr Val Glu Thr Leu Met Leu His Pro Val Ile Lys Ala Phe Leu
            20                  25                  30

Cys Gly Ser Ile Ser Gly Thr Cys Ser Thr Leu Leu Phe Gln Pro Leu
        35                  40                  45

Asp Leu Leu Lys Thr Arg Leu Gln Thr Leu Gln Pro Ser Asp His Gly
    50                  55                  60

Ser Arg Arg Val Gly Met Leu Ala Val Leu Leu Lys Val Val Arg Thr
65                  70                  75                  80

Glu Ser Leu Leu Gly Leu Trp Lys Gly Met Ser Pro Ser Ile Val Arg
                85                  90                  95

Cys Val Pro Gly Val Gly Ile Tyr Phe Gly Thr Leu Tyr Ser Leu Lys
            100                 105                 110

Gln Tyr Phe Leu Arg Gly His Pro Pro Thr Ala Leu Glu Ser Val Met
        115                 120                 125

Leu Gly Val Gly Ser Arg Ser Val Ala Gly Val Cys Met Ser Pro Ile
    130                 135                 140

Thr Val Ile Lys Thr Arg Tyr Glu Ser Gly Lys Tyr Gly Tyr Glu Ser
145                 150                 155                 160

Ile Tyr Ala Ala Leu Arg Ser Ile Tyr His Ser Glu Gly His Arg Gly
                165                 170                 175

Leu Phe Ser Gly Leu Thr Ala Thr Leu Leu Arg Asp Ala Pro Phe Ser
            180                 185                 190

Gly Ile Tyr Leu Met Phe Tyr Asn Gln Thr Lys Asn Ile Val Pro His
        195                 200                 205

Asp Gln Val Asp Ala Thr Leu Ile Pro Ile Thr Asn Phe Ser Cys Gly
    210                 215                 220

Ile Phe Ala Gly Ile Leu Ala Ser Leu Val Thr Gln Pro Ala Asp Val
225                 230                 235                 240

Ile Lys Thr His Met Gln Leu Tyr Pro Leu Lys Phe Gln Trp Ile Gly
                245                 250                 255

Gln Ala Val Thr Leu Ile Phe Lys Asp Tyr Gly Leu Arg Gly Phe Phe
            260                 265                 270

Gln Gly Gly Ile Pro Arg Ala Leu Arg Arg Thr Leu Met Ala Ala Met
        275                 280                 285

Ala Trp Thr Val Tyr Glu Glu Met Met Ala Lys Met Gly Leu Lys Ser
    290                 295                 300


<210> SEQ ID NO 3
<211> LENGTH: 714
<212> TYPE: DNA
<213> ORGANISM: Homo sapiens

<400> SEQUENCE: 3

atgattcaga actcacgtcc gtcgctgctg caaccccaag atgtcggaga cacggtggaa      60
```

acgcttatgt tacatccggt gatcaaggct ttcctgtgtg gctccatcag tgggacctgc 120
tctaccctcc ttttccaacc tctggatctc cttaaaacac gcctgcaaac cctccagccc 180
tcagatcatg ggtctagacg tgttgggatg ttggctgtac tcttgaaggt ggttcgcacg 240
gagagtcttt tgggcctttg gaaagggatg tccccttcca ttgtgagatg tgtccctggc 300
gttggaatct actttggcac tctctactct ttgaagcagt atttcttgcg aggccatccc 360
ccaaccgccc tggagtcagt catgctgggg gtgggctctc gctctgttgc aggggtctgt 420
atgtcaccta tcactgtaat caagacgcgc tatgagagtg ggaaatatgg ctatgagagt 480
atctacgctg ccctgaggag catctatcac agtgaggggc accggggcct cttcagtggc 540
ctgacagcaa ctctccttcg agatgcgccc ttctcaggaa tctacctgat gttttacaac 600
cagaccaaaa atatagtgcc tcatggacta tggactacgt ggcttcttcc aaggtggcat 660
cccccgagcc ctccgcagaa ctctaatggc agcaatggcg tggacggtgt atga 714

<210> SEQ ID NO 4
<211> LENGTH: 915
<212> TYPE: DNA
<213> ORGANISM: Homo sapiens

<400> SEQUENCE: 4
atgattcaga actcacgtcc gtcgctgctg caaccccaag atgtcggaga cacggtggaa 60
acgcttatgt tacatccggt gatcaaggct ttcctgtgtg gctccatcag tgggacctgc 120
tctaccctcc ttttccaacc tctggatctc cttaaaacac gcctgcaaac cctccagccc 180
tcagatcatg ggtctagacg tgttgggatg ttggctgtac tcttgaaggt ggttcgcacg 240
gagagtcttt tgggcctttg gaaagggatg tccccttcca ttgtgagatg tgtccctggc 300
gttggaatct actttggcac tctctactct ttgaagcagt atttcttgcg aggccatccc 360
ccaaccgccc tggagtcagt catgctgggg gtgggctctc gctctgttgc aggggtctgt 420
atgtcaccta tcactgtaat caagacgcgc tatgagagtg ggaaatatgg ctatgagagt 480
atctacgctg ccctgaggag catctatcac agtgaggggc accggggcct cttcagtggc 540
ctgacagcaa ctctccttcg agatgcgccc ttctcaggaa tctacctgat gttttacaac 600
cagaccaaaa atatagtgcc tcatgaccag gtggatgcaa cccttattcc tattacaaat 660
ttcagctgtg ggatatttgc tggtattctg gcctcactgg taactcaacc tgcggatgtt 720
atcaaaactc atatgcagct ttatccactg aagtttcaat ggattggcca agcagtgaca 780
cttattttca aagactatgg actacgtggc ttcttccaag gtggcatccc ccgagccctc 840
cgcagaactc taatggcagc aatggcgtgg acggtgtatg aagagatgat ggccaagatg 900
ggcctgaagt cctga 915

<210> SEQ ID NO 5
<211> LENGTH: 587
<212> TYPE: PRT
<213> ORGANISM: Homo sapiens

<400> SEQUENCE: 5

Met Val Thr Ala Ala Met Leu Leu Gln Cys Cys Pro Val Leu Ala Arg
1               5                   10                  15

Gly Pro Thr Ser Leu Leu Gly Lys Val Val Lys Thr His Gln Phe Leu
            20                  25                  30

Phe Gly Ile Gly Arg Cys Pro Ile Leu Ala Thr Gln Gly Pro Asn Cys
        35                  40                  45

-continued

```
Ser Gln Ile His Leu Lys Ala Thr Lys Ala Gly Gly Asp Ser Pro Ser
    50                  55                  60

Trp Ala Lys Gly His Cys Pro Phe Met Leu Ser Glu Leu Gln Asp Gly
65                  70                  75                  80

Lys Ser Lys Ile Val Gln Lys Ala Ala Pro Glu Val Gln Glu Asp Val
                85                  90                  95

Lys Ala Phe Lys Thr Asp Leu Pro Ser Ser Leu Val Ser Val Ser Leu
            100                 105                 110

Arg Lys Pro Phe Ser Gly Pro Gln Glu Gln Glu Gln Ile Ser Gly Lys
        115                 120                 125

Val Thr His Leu Ile Gln Asn Asn Met Pro Gly Asn Tyr Val Phe Ser
    130                 135                 140

Tyr Asp Gln Phe Phe Arg Asp Lys Ile Met Glu Lys Lys Gln Asp His
145                 150                 155                 160

Thr Tyr Arg Val Phe Lys Thr Val Asn Arg Trp Ala Asp Ala Tyr Pro
                165                 170                 175

Phe Ala Gln His Phe Ser Glu Ala Ser Val Ala Ser Lys Asp Val Ser
            180                 185                 190

Val Trp Cys Ser Asn Asp Tyr Leu Gly Met Ser Arg His Pro Gln Val
        195                 200                 205

Leu Gln Ala Thr Gln Glu Thr Leu Gln Arg His Gly Ala Gly Ala Gly
    210                 215                 220

Gly Thr Arg Asn Ile Ser Gly Thr Ser Lys Phe His Val Glu Leu Glu
225                 230                 235                 240

Gln Glu Leu Ala Glu Leu His Gln Lys Asp Ser Ala Leu Leu Phe Ser
                245                 250                 255

Ser Cys Phe Val Ala Asn Asp Ser Thr Leu Phe Thr Leu Ala Lys Ile
            260                 265                 270

Leu Pro Gly Cys Glu Ile Tyr Ser Asp Ala Gly Asn His Ala Ser Met
        275                 280                 285

Ile Gln Gly Ile Arg Asn Ser Gly Ala Ala Lys Phe Val Phe Arg His
    290                 295                 300

Asn Asp Pro Asp His Leu Lys Lys Leu Leu Glu Lys Ser Asn Pro Lys
305                 310                 315                 320

Ile Pro Lys Ile Val Ala Phe Glu Thr Val His Ser Met Asp Gly Ala
                325                 330                 335

Ile Cys Pro Leu Glu Glu Leu Cys Asp Val Ser His Gln Tyr Gly Ala
            340                 345                 350

Leu Thr Phe Val Asp Glu Val His Ala Val Gly Leu Tyr Gly Ser Arg
        355                 360                 365

Gly Ala Gly Ile Gly Glu Arg Asp Gly Ile Met His Lys Ile Asp Ile
    370                 375                 380

Ile Ser Gly Thr Leu Gly Lys Ala Phe Gly Cys Val Gly Gly Tyr Ile
385                 390                 395                 400

Ala Ser Thr Arg Asp Leu Val Asp Met Val Arg Ser Tyr Ala Ala Gly
                405                 410                 415

Phe Ile Phe Thr Thr Ser Leu Pro Pro Met Val Leu Ser Gly Ala Leu
            420                 425                 430

Glu Ser Val Arg Leu Leu Lys Gly Glu Glu Gly Gln Ala Leu Arg Arg
        435                 440                 445

Ala His Gln Arg Asn Val Lys His Met Arg Gln Leu Leu Met Asp Arg
    450                 455                 460
```

```
Gly Leu Pro Val Ile Pro Cys Pro Ser His Ile Ile Pro Ile Arg Val
465                 470                 475                 480

Gly Asn Ala Ala Leu Asn Ser Lys Leu Cys Asp Leu Leu Leu Ser Lys
                485                 490                 495

His Gly Ile Tyr Val Gln Ala Ile Asn Tyr Pro Thr Val Pro Arg Gly
            500                 505                 510

Glu Glu Leu Leu Arg Leu Ala Pro Ser Pro His His Ser Pro Gln Met
        515                 520                 525

Met Glu Asp Phe Val Glu Lys Leu Leu Leu Ala Trp Thr Ala Val Gly
    530                 535                 540

Leu Pro Leu Gln Asp Val Ser Val Ala Ala Cys Asn Phe Cys Arg Arg
545                 550                 555                 560

Pro Val His Phe Glu Leu Met Ser Glu Trp Glu Arg Ser Tyr Phe Gly
                565                 570                 575

Asn Met Gly Pro Gln Tyr Val Thr Thr Tyr Ala
            580                 585


<210> SEQ ID NO 6
<211> LENGTH: 1764
<212> TYPE: DNA
<213> ORGANISM: Homo sapiens

<400> SEQUENCE: 6

atggtgactg cagccatgct gctacagtgc tgcccagtgc ttgcccgggg ccccacaagc      60

ctcctaggca aggtggttaa gactcaccag ttcctgtttg gtattggacg ctgtcccatc     120

ctggctaccc aaggaccaaa ctgttctcaa atccacctta aggcaacaaa ggctggagga     180

gattctccat cttgggcgaa gggccactgt cccttcatgc tgtcggaact ccaggatggg     240

aagagcaaga ttgtgcagaa ggcagcccca gaagtccagg aagatgtgaa ggctttcaag     300

acagatctgc ctagctccct ggtctcagtc agcctaagga agccattttc cggtccccag     360

gagcaggagc agatctctgg gaaggtcaca cacctgattc agaacaatat gcctggaaac     420

tatgtcttca gttatgacca gtttttcagg gacaagatca tggagaagaa acaggatcac     480

acctaccgtg tgttcaagac tgtgaaccgc tgggctgatg catatccctt tgcccaacat     540

ttctctgagg catctgtggc ctcaaaggat gtgtccgtct ggtgtagtaa tgattacctg     600

ggcatgagcc gacaccctca ggtcttgcaa gccacacagg agaccctgca gcgtcatggt     660

gctggagctg gtggcacccg caacatctca ggcaccagta agtttcatgt ggagcttgag     720

caggagctgg ctgagctgca ccagaaggac tcagccctgc tcttctcctc ctgctttgtt     780

gccaatgact ctactctctt caccttggcc aagatcctgc cagggtgcga gatttactca     840

gacgcaggca accatgcttc catgatccaa ggtatccgta acagtggagc agccaagttt     900

gtcttcaggc acaatgaccc tgaccaccta aagaaacttc tagagaagtc taaccctaag     960

atacccaaaa ttgtggcctt tgagactgtc cactccatgg atggtgccat ctgtcccctc    1020

gaggagttgt gtgatgtgtc ccaccagtat ggggccctga ccttcgtgga tgaggtccat    1080

gctgtaggac tgtatgggtc ccggggcgct gggattgggg agcgtgatgg aattatgcat    1140

aagattgaca tcatctctgg aactcttggc aaggcctttg gctgtgtggg cggctacatt    1200

gccagcaccc gtgacttggt ggacatggtg cgctcctatg ctgcaggctt catctttacc    1260

acttctctgc cccccatggt gctctctgga gctctagaat ctgtgcggct gctcaaggga    1320

gaggagggcc aagccctgag gcgagcccac cagcgcaatg tcaagcacat gcgccagcta    1380

ctcatggaca ggggccttcc tgtcatcccc tgccccagcc acatcatccc catccgggtg    1440
```

ggcaatgcag cactcaacag caagctctgt gatctcctgc tctccaagca tggcatctat 1500
gtgcaggcca tcaactaccc aactgtcccc cggggtgaag agctcctgcg cttggcaccc 1560
tccccccacc acagccctca gatgatggaa gattttgtgg agaagctgct gctggcttgg 1620
actgcggtgg ggctgcccct ccaggatgtg tctgtggctg cctgcaattt ctgtcgccgt 1680
cctgtacact ttgagctcat gagtgagtgg gaacgttcct acttcgggaa catggggccc 1740
cagtatgtca ccacctatgc ctga 1764

<210> SEQ ID NO 7
<211> LENGTH: 14135
<212> TYPE: DNA
<213> ORGANISM: Artificial Sequence
<220> FEATURE:
<223> OTHER INFORMATION: vector ALS17

<400> SEQUENCE: 7
ctgtcagacc aagtttactc atatatactt tagattgatt taaaacttca tttttaattt 60
aaaaggatct aggtgaagat cctttttgat aatctcatga ccaaaatccc ttaacgtgag 120
ttttcgttcc actgagcgtc agaccccgta gaaaagatca aaggatcttc ttgagatcct 180 tttttctgc gcgtaatctg ctgcttgcaa acaaaaaaac caccgctacc agcggtggtt 240
tgtttgccgg atcaagagct accaactctt tttccgaagg taactggctt cagcagagcg 300
cagataccaa atactgtcct tctagtgtag ccgtagttag gccaccactt caagaactct 360
gtagcaccgc ctacatacct cgctctgcta atcctgttac cagtggctgc tgccagtggc 420
gataagtcgt gtcttaccgg gttggactca agacgatagt taccggataa ggcgcagcgg 480
tcgggctgaa cggggggttc gtgcacacag cccagcttgg agcgaacgac ctacaccgaa 540
ctgagatacc tacagcgtga gctatgagaa agcgccacgc ttcccgaagg gagaaaggcg 600
gacaggtatc cggtaagcgg cagggtcgga acaggagagc gcacgaggga gcttccaggg 660
ggaaacgcct ggtatcttta tagtcctgtc gggtttcgcc acctctgact tgagcgtcga 720
tttttgtgat gctcgtcagg ggggcggagc ctatggaaaa acgccagcaa cgcggccttt 780
ttacggttcc tggccttttg ctggcctttt gctcacatgt tctttcctgc gttatcccct 840
gattctgtgg ataaccgtat taccgccttt gagtgagctg ataccgctcg ccgcagccga 900
acgaccgagc gcagcgagtc agtgagcgag gaagcggaag agcgcccaat acgcaaaccg 960
cctctccccg cgcgttggcc gattcattaa tgcagctggc acgacaggtt tcccgactgg 1020
aaagcgggca gtgagcgcaa cgcaattaat gtgagttagc tcactcatta ggcaccccag 1080
gctttacact ttatgcttcc ggctcgtatg ttgtgtggaa ttgtgagcgg ataacaattt 1140
cacacaggaa acagctatga ccatgattac gccaagcgcg caattaaccc tcactaaagg 1200
gaacaaaagc tggagctgca agcttggcca ttgcatacgt tgtatccata tcataatatg 1260
tacatttata ttggctcatg tccaacatta ccgccatgtt gacattgatt attgactagt 1320
tattaatagt aatcaattac ggggtcatta gttcatagcc catatatgga gttccgcgtt 1380
acataactta cggtaaatgg cccgcctggc tgaccgccca acgacccccg cccattgacg 1440
tcaataatga cgtatgttcc catagtaacg ccaataggga ctttccattg acgtcaatgg 1500
gtggagtatt tacggtaaac tgcccacttg gcagtacatc aagtgtatca tatgccaagt 1560
acgcccccta ttgacgtcaa tgacggtaaa tggcccgcct ggcattatgc ccagtacatg 1620
accttatggg actttcctac ttggcagtac atctacgtat tagtcatcgc tattaccatg 1680

-continued

```
gtgatgcggt tttggcagta catcaatggg cgtggatagc ggtttgactc acggggattt   1740
ccaagtctcc accccattga cgtcaatggg agtttgtttt ggcaccaaaa tcaacgggac   1800
tttccaaaat gtcgtaacaa ctccgcccca ttgacgcaaa tgggcggtag gcgtgtacgg   1860
tgggaggtct atataagcag agctcgttta gtgaaccggg gtctctctgg ttagaccaga   1920
tctgagcctg ggagctctct ggctaactag ggaacccact gcttaagcct caataaagct   1980
tgccttgagt gcttcaagta gtgtgtgccc gtctgttgtg tgactctggt aactagagat   2040
ccctcagacc cttttagtca gtgtggaaaa tctctagcag tggcgcccga acagggacct   2100
gaaagcgaaa gggaaaccag agctctctcg acgcaggact cggcttgctg aagcgcgcac   2160
ggcaagaggc gaggggcggc gactggtgag tacgccaaaa attttgacta gcggaggcta   2220
gaaggagaga gatgggtgcg agagcgtcag tattaagcgg gggagaatta gatcgcgatg   2280
ggaaaaaatt cggttaaggc cagggggaaa gaaaaaatat aaattaaaac atatagtatg   2340
ggcaagcagg gagctagaac gattcgcagt taatcctggc ctgttagaaa catcagaagg   2400
ctgtagacaa atactgggac agctacaacc atcccttcag acaggatcag aagaacttag   2460
atcattatat aatacagtag caaccctcta ttgtgtgcat caaaggatag agataaaaga   2520
caccaaggaa gctttagaca agatagagga agagcaaaac aaaagtaaga ccaccgcaca   2580
gcaagcggcc gctgatcttc agacctggag gaggagatat gagggacaat tggagaagtg   2640
aattatataa atataaagta gtaaaaattg aaccattagg agtagcaccc accaaggcaa   2700
agagaagagt ggtgcagaga gaaaaaagag cagtgggaat aggagctttg ttccttgggt   2760
tcttgggagc agcaggaagc actatgggcg cagcctcaat gacgctgacg gtacaggcca   2820
gacaattatt gtctggtata gtgcagcagc agaacaattt gctgagggct attgaggcgc   2880
aacagcatct gttgcaactc acagtctggg gcatcaagca gctccaggca agaatcctgg   2940
ctgtggaaag atacctaaag gatcaacagc tcctggggat ttggggttgc tctggaaaac   3000
tcatttgcac cactgctgtg ccttggaatg ctagttggag taataaatct ctggaacaga   3060
tttggaatca cacgacctgg atggagtggg acagagaaat taacaattac acaagcttaa   3120
tacactcctt aattgaagaa tcgcaaaacc agcaagaaaa gaatgaacaa gaattattgg   3180
aattagataa atgggcaagt ttgtggaatt ggtttaacat aacaaattgg ctgtggtata   3240
taaaattatt cataatgata gtaggaggct tggtaggttt aagaatagtt tttgctgtac   3300
tttctatagt gaatagagtt aggcagggat attcaccatt atcgtttcag acccacctcc   3360
caaccccgag gggacccgac aggcccgaag gaatagaaga agaaggtgga gagagagaca   3420
gagacagatc cattcgatta gtgaacggat ctcgacggta tcggttaact tttaaaagaa   3480
aaggggggat tggggggtac agtgcagggg aaagaatagt agacataata gcaacagaca   3540
tacaaactaa agaattacaa aaacaaatta caaaaattca aaattttatc gataagcttg   3600
ggagttccgc gtgttggggg tggaccatcc tctaggtatt gaataagaaa aatgaagtta   3660
aggtggttga tggtaacact atgctaataa ctgcagagcc agaagcacca taagggacat   3720
gataagggag ccagcagacc tctgatctct tcctgaatgc taatcttaaa catcctgagg   3780
aagaatggga cttccatttg gggtgggcct atgatagggt aataagacag tagtgaatat   3840
caagctacaa aaagccccct ttcaaattct tctcagtcct aacttttcat actaagccca   3900
gtccttccaa agcagactgt gaaagagtga tagttccggg agactagcac tgcagattcc   3960
gggtcactgt gagtggggga ggcagggaag aagggctcac aggacagtca aaccatgccc   4020
cctgtttttc cttcttcaag tagacctcta taagacaaca gagacaacta aggctgagtg   4080
```

```
gccaggcgag gagaaaccat ctcgccgtaa aacatggaag gaacacttca ggggaaaggt   4140
ggtatctcta agcaagagaa ctgagtggag tcaaggctga gagatgcagg ataagcaaat   4200
gggtagtgaa aagacattca tgaggacagc taaaacaata agtaatgtaa aatacagcat   4260
agcaaaactt taacctccaa atcaagcctc tacttgaatc cttttctgag ggatgaataa   4320
ggcataggca tcaggggctg ttgccaatgt gcattagctg tttgcagcct caccttcttt   4380
catggagttt aagatatagt gtattttccc aaggtttgaa ctagctcttc atttctttat   4440
gttttaaatg cactgacctc ccacattccc tttttagtaa aatattcaga aataatttaa   4500
atacatcatt gcaatgaaaa taaatgtttt ttattaggca gaatccagat gctcaaggcc   4560
cttcataata tcccccagtt tagtagttgg acttagggaa caaaggaacc tttaatagaa   4620
attggacagc aagaaagcga gcttagtgat acttgtgggc cagggcatta gccacaccag   4680
ccaccacttt ctgataggca gcctgcactg gtggggtgaa ttctttgcca aagtgatggg   4740
ccagcacaca gaccagcacg ttgcccagga gctgtgggag gaagataaga ggtatgaaca   4800
tgattagcaa aagggcctag cttggactca gaataatcca gccttatccc aaccataaaa   4860
taaaagcaga atggtagctg gattgtagct gctattagca atatgaaacc tcttacatca   4920
gttacaattt atatgcagaa atatttatat gcagaaatat tgctattgcc ttaacccaga   4980
aattatcact gttattcttt agaatggtgc aaagaggcat gatacattgt atcattattg   5040
ccctgaaaga aagagattag ggaaagtatt agaaataaga taaacaaaaa agtatattaa   5100
aagaagaaag catttttttaa aattacaaat gcaaaattac cctgatttgg tcaatatgtg   5160
tacacatatt aaaacattac actttaaccc ataaatatgt ataatgatta tgtatcaatt   5220
aaaaataaaa gaaaataaag tagggagatt atgaatatgc aaataagcac acatatattc   5280
caaatagtaa tgtactaggc agactgtgta aagttttttt ttaagttact taatgtatct   5340
cagagatatt tccttttgtt atacacaatg ttaaggcatt aagtataata gtaaaaattg   5400
cggagaagaa aaaaaaagaa agcaagaatt aaacaaaaga aaacaattgt tatgaacagc   5460
aaataaaaga aactaaaacg atcctgagac ttccacactg atgcaatcat tcgtctgttt   5520
cccattctaa actgtaccct gttacttctc cccttcctat gacatgaact taaccataga   5580
aaagaagggg aaagaaaaca tcaagggtcc catagactca ccctgaagtt ctcaggatcc   5640
acgtgcagct tgtcacagtg cagctcactc actgtggcaa aggtgccctt gaggttgtcc   5700
aggtgagcca ggccatcact aaaggcaccg agcactttct tgccatgagc cttcacctta   5760
gggttgccca taacagcatc aggagtggac agatccccaa aggactcaaa gaacctctgg   5820
gtccaagggt agaccaccag cagcctaagg gtgggaaaat agaccaatag gcagagagag   5880
tcagtgccta tcagaaaccc aagagtcttc tctgtctcca catgcccagt ttctattggt   5940
ctccttaaac ctgtcttgta accttgatac caacctgccc agggcctcac caccaacttc   6000
atccacgttc accttgcccc acagggcagt aacggcagac ttctcctcag gagtcaggtg   6060
caccatggtg tctgtttgag gttgctagtg aacacagttg tgtcagaagc aaatgtaagc   6120
aatagatggc tctgccctga cttttatgcc cagccctggc tcctgccctc cctgctcctg   6180
ggagtagatt ggccaaccct agggtgtggc tccacagggt gaggtctaag tgatgacagc   6240
cgtacctgtc cttggctctt ctggcactgg cttaggagtt ggacttcaaa ccctcagccc   6300
tccctctaag atatatctct tggccccata ccatcagtac aaattgctac taaaaacatc   6360
ctcctttgca agtgtattta cgtaatattt ggaatcacag cttggtaagc atattgaaga   6420
```

-continued

```
tcgttttccc aattttctta ttacacaaat aagaaattga tgcactaaaa gtggaagagt   6480
tttgtctacc ataattcagc tttgggatat gtagatggat ctcttcctgc gtctccagaa   6540
tatgcaaaat acttacagga cagaatggat gaaaactcta cctcagttct aagcatatct   6600
tctccttatt tggattaaaa ccttctggta agaaaagaaa aaaaatatat atatatatgt   6660
gtatatatac acacatacat atacatatat atgcattcat ttgttgttgt ttttcttaat   6720
ttgctcatgg tatatgtgta tatatatata tatatattca ggaaataata tattctagac   6780
tcaagcctca ttcagacact agtgtcacca gtctcctcat atacctattg tattttcttc   6840
ttcttgctgg tttagtcatg ttttctggga gcttaggggc ttattttatt ttgttttgtt   6900
ttctaatcaa cagagatggg caaacccatt atttttttct ttagacttgg gatggtgata   6960
gctgggcagc gtcagaaact gtgtgtggat atagataaga gctcaggact atgctgagct   7020
gtgatgaggg aggggcctag ctaaaggcag tgagagtcag aatgctcctg ctattgcctt   7080
ctcagtcccc acgcttggtt tctacacaag tagatacata gaaaaggcta taggttagtg   7140
tttgagagtc ctgcatgatt agttgctcag aaatgcccga taaatatgtt atgtgtgttt   7200
atgtatatat atgttttata tatatatata tgtgtgtgtg tgtgtgtgtg tgtgttgtgt   7260
ttacaaatat gtgattatca tcaaaacgtg agggctaaag tgaccagata acttgcaagt   7320
cctaggatac caggaaatct agaatatgtc acattctgtc tcaggcatcc atttcttta    7380
tgatgccgtt tgaggtggag ttttagtcag gtggtcagct tctccttttt tttgccatct   7440
gccctgtaag catcctgctg gggacccaga taggagtcat cactctaggc tgagaacatc   7500
tgggcacaca ccctaagcct cagcatgact catcatgact cagcattgct gtgcttgagc   7560
cagaaggttt gcttagaagg ttacacagaa ccagaaggcg ggggtggggc actgaccccg   7620
acaggggcct ggccagaact gctcatgctt ggactatggg aggtcactaa tggagacaca   7680
cagaaatgta acaggaacta aggaaaaact gaagcttatt taatcagaga tgagatgctg   7740
gaagggatag agggagctga gcttgtaaaa agtatagtaa tcattcagca aatggttttg   7800
aagcacctgc tggatgctaa acactatttt cagtgcttga atcataaata agaataaaac   7860
atgtatctta ttccccacaa gagtccaagt aaaaaataac agttaattat aatgtgctct   7920
gtcccccagg ctggagtgca gtggcacgat ctcagctcac tgcaacctcc gcctcccggg   7980
ttcaagcaat tctcctgcct cagccaccct aatagctggg attacaggtg cacaccacca   8040
tgccaggcta atttttgtac tttttgtaga ggcagggtat caccatgttg tccaagatgg   8100
tcttgaactc ctgagctcca agcagtccac ccacctcagc ctcccaaagt gctatctgcg   8160
gccgcctatc tgtaccacta gtctcgagaa gctttcatta aaaaaagtct aaccagctgc   8220
attcgacttt gactgcagca gctggttaga aggttctact ggaggagggt cccagcccat   8280
tgctaaatta acatcaggct ctgagactgg cagtatatct ctaacagtgg ttgatgctat   8340
cttctggaac ttgcctgcta cattgagacc actgacccat acataggaag cccatagctc   8400
tgtcctgaac tgttaggcca ctggtccaga gagtgtgcat ctcctttgat cctcataata   8460
accctatgag atagacacaa ttattactct tactttatag atgatgatcc tgaaaacata   8520
ggagtcaagg cacttgcccc tagctggggg tataggggag cagtcccatg tagtagtaga   8580
atgaaaaatg ctgctatgct gtgcctcccc cacctttccc atgtctgccc tctactcatg   8640
gtctatctct cctggctcct gggagtcatg gactccaccc agcaccacca acctgaccta   8700
accacctatc tgagcctgcc agcctataac ccatctgggc cctgatagct ggtggccagc   8760
cctgacccca ccccaccctc cctggaacct ctgatagaca catctggcac accagctcgc   8820
```

```
aaagtcaccg tgagggtctt gtgtttgctg agtcaaaatt ccttgaaatc caagtcctta   8880
gagactcctg ctcccaaatt tacagtcata gacttcttca tggctgtctc ctttatccac   8940
agaatgattc ctttgcttca ttgccccatc catctgatcc tcctcatcag tgcagcacag   9000
ggcccatgag cagtagctgc agagtctcac ataggtctgg cactgcctct gacatgtccg   9060
accttaggca aatgcttgac tcttctgagc tcagtcttgt catggcaaaa taaagataat   9120
aatagtgttt ttttatggag ttagcgtgag gatggaaaac aatagcaaaa ttgattagac   9180
tataaaaggt ctcaacaaat agtagtagat tttatcatcc attaatcctt ccctctcctc   9240
tcttactcat cccatcacgt atgcctctta attttccctt acctataata agagttattc   9300
ctcttattat attcttctta tagtgattct ggatattaaa gtgggaatga ggggcaggcc   9360
actaacgaag aagatgtttc tcaaagaagc cattctcccc acatagatca tctcagcagg   9420
gttcaggaag ataaaggagg atcaaggtcg aaggtaggaa ctaaggaaga acactgggac   9480
cggtactagt gcatgcaaat ctgacactca gtgggcctgg gtgaaggtga gaattttatt   9540
gctgaatgag agcctctggg gacatcttgc cagtcaatga gtctcaggtt caatttcctt   9600
ctcagtcttg gagtaacaga agctcatgca tttaataaac ggaaattttg tattgaaatg   9660
agagccattg gaaatcattt actccagact cctacttata aaaagagaaa ctgaggctca   9720
gagaagggtg gggactttct cagtatgaca tggaaatgat caggcttgga ttcaaagctc   9780
ctgactttct gtctagtgta tgtgcagtga gccccttttc ctctaactga aagaaggaaa   9840
aaaaaatgga acccaaaata ttctacatag tttccatgtc acagccaggg ctgggcagtc   9900
tcctgttatt tcttttaaaa taaatatatc atttaaatgc ataaataagc aaaccctgct   9960
cgggaatggg agggagagtc tctggagtcc accccttctc ggccctggct ctgcagatag  10020
tgctatcaaa gccctgacag agccctgccc attgctgggc cttggagtga gtcagcctag  10080
tagagaggca gggcaagcca tctcatagct gctgagtggg agagagaaaa gggctcattg  10140
tctataaact caggtcatgg ctattcttat tctcacacta agaaaaagaa tgagatgtct  10200
acatataccc tgcgtcccct cttgtgtact ggggtcccca agagctctct aaaagtgatg  10260
gcaaagtcat tgcgctagat gccatcccat ctattataaa cctgcatttg tctccacaca  10320
ccagtcatgg acaataaccc tcctcccagg tccacgtgct tgtctttgta taatactcaa  10380
gtaatttcgg aaaatgtatt ctttcaatct tgttctgtta ttcctgtttc aatggcttag  10440
tagaaaaagt acatacttgt tttcccataa attgacaata gacaatttca catcaatgtc  10500
tatatgggtc gttgtgtttg ctgtgtttgc aaaaactcac aataacttta tattgttact  10560
actctaagaa agttacaaca tggtgaatac aagagaaagc tattacaagt ccagaaaata  10620
aaagttatca tcttgaggcc tcctgcaggg tacctttaag accaatgact tacaaggcag  10680
ctgtagatct tagccacttt ttaaaagaaa aggggggact ggaagggcta attcactccc  10740
aacgaagaca agatctgctt tttgctgtgc gggccaggcc cccgagggcc ttatcggccc  10800
cagaggcgct tgctgtcggg ccgggcgctc ccggcacggg cgggcggagg ggtggcgccc  10860
gcctggggac cgcagattac aagagcacct cctcccccaa ccccaggagg ccccgctccc  10920
caggcctcgg ccggcgcgga cccctggttg ccccggactg ggtctctctg gttagaccag  10980
atctgagcct gggagctctc tggctaacta gggaacccac tgcttaagcc tcaataaagc  11040
ttgccttgag tgcttcaagt agtgtgtgcc cgtctgttgt gtgactctgg taactagaga  11100
tccctcagac ccttttagtc agtgtggaaa atctctagca ggctagcaaa caaaagacgt  11160
```

-continued

```
acgagctatg ctttaattaa agctatgctg tcgacaatca acctctggat tacaaaattt  11220
gtgaaagatt gactggtatt cttaactatg ttgctccttt tacgctatgt ggatacgctg  11280
ctttaatgcc tttgtatcat gctattgctt cccgtatggc tttcattttc tcctccttgt  11340
ataaatcctg gttgctgtct ctttatgagg agttgtggcc cgttgtcagg caacgtggcg  11400
tggtgtgcac tgtgtttgct gacgcaaccc ccactggttg gggcattgcc accacctgtc  11460
agctcctttc cgggactttc gctttccccc tccctattgc cacggcggaa ctcatcgccg  11520
cctgccttgc ccgctgctgg acaggggctc ggctgttggg cactgacaat tccgtggtgt  11580
tgtcggggaa gctgacgtcc tttccatggc tgctcgcctg tgttgccacc tggattctgc  11640
gcgggacgtc cttctgctac gtcccttcgg ccctcaatcc agcggacctt ccttcccgcg  11700
gcctgctgcc ggctctgcgg cctcttccgc gtcttcgcct tcgccctcag acgagtcgga  11760
tctccctttg ggccgcctcc ccgcctggaa ttcgagctcg gtacctgatc agcctcgact  11820
gtgccttcta gttgccagcc atctgttgtt tgcccctccc ccgtgccttc cttgaccctg  11880
gaaggtgcca ctcccactgt cctttcctaa taaaatgagg aaattgcatc gcattgtctg  11940
agtaggtgtc attctattct ggggggtggg gtggggcagg acagcaaggg ggaggattgg  12000
gaagacaata gcaggcatgc tggggatgcg gtgggctcta tggcttctga ggaaagaacc  12060
agctggggct cgagatccac tagttctagc ctcgaggcta gagcggccgc caccgcggta  12120
gtagttcatg tcatcttatt attcagtatt tataacttgc aaagaaatga atatcagaga  12180
gtgagaggaa cttgtttatt gcagcttata atggttacaa ataaagcaat agcatcacaa  12240
atttcacaaa taaagcattt ttttcactgc attctagttg tggtttgtcc aaactcatca  12300
atgtatctta tcatgtctgg ctctagctat cccgccccta actccgccca gttccgccca  12360
ttctccgccc catggctgac taattttttt tatttatgca gaggccgagg ccgcctcggc  12420
ctctgagcta ttccagaagt agtgaggagg cttttttgga ggcctaggct tttgcgtcga  12480
gacgtaccca attcgcccta tagtgagtcg tattacgcgc gctcactggc cgtcgtttta  12540
caacgtcgtg actgggaaaa ccctggcgtt acccaactta atcgccttgc agcacatccc  12600
cctttcgcca gctggcgtaa tagcgaagag gcccgcaccg atcgcccttc ccaacagttg  12660
cgcagcctga atggcgaatg gcgcgacgcg ccctgtagcg gcgcattaag cgcggcgggt  12720
gtggtggtta cgcgcagcgt gaccgctaca cttgccagcg ccctagcgcc cgctcctttc  12780
gctttcttcc cttcctttct cgccacgttc gccggctttc cccgtcaagc tctaaatcgg  12840
gggctccctt tagggttccg atttagtgct ttacggcacc tcgaccccaa aaaacttgat  12900
tagggtgatg gttcacgtag tgggccatcg ccctgataga cggtttttcg ccctttgacg  12960
ttggagtcca cgttctttaa tagtggactc ttgttccaaa ctggaacaac actcaaccct  13020
atctcggtct attcttttga tttataaggg attttgccga tttcggccta ttggttaaaa  13080
aatgagctga tttaacaaaa atttaacgcg aattttaaca aaatattaac gtttacaatt  13140
tcccaggtgg cacttttcgg ggaaatgtgc gcggaacccc tatttgttta tttttctaaa  13200
tacattcaaa tatgtatccg ctcatgagac aataaccctg ataaatgctt caataatatt  13260
gaaaaaggaa gagtatgagt attcaacatt tccgtgtcgc ccttattccc ttttttgcgg  13320
cattttgcct tcctgttttt gctcacccag aaacgctggt gaaagtaaaa gatgctgaag  13380
atcagttggg tgcacgagtg ggttacatcg aactggatct caacagcggt aagatccttg  13440
agagttttcg ccccgaagaa cgttttccaa tgatgagcac ttttaaagtt ctgctatgtg  13500
gcgcggtatt atcccgtatt gacgccgggc aagagcaact cggtcgccgc atacactatt  13560
```

-continued

```
ctcagaatga cttggttgag tactcaccag tcacagaaaa gcatcttacg gatggcatga  13620

cagtaagaga attatgcagt gctgccataa ccatgagtga taacactgcg gccaacttac  13680

ttctgacaac gatcggagga ccgaaggagc taaccgcttt tttgcacaac atgggggatc  13740

atgtaactcg ccttgatcgt tgggaaccgg agctgaatga agccatacca aacgacgagc  13800

gtgacaccac gatgcctgta gcaatggcaa caacgttgcg caaactatta actggcgaac  13860

tacttactct agcttcccgg caacaattaa tagactggat ggaggcggat aaagttgcag  13920

gaccacttct gcgctcggcc cttccggctg gctggtttat tgctgataaa tctggagccg  13980

gtgagcgtgg gtctcgcggt atcattgcag cactggggcc agatggtaag ccctcccgta  14040

tcgtagttat ctacacgacg gggagtcagg caactatgga tgaacgaaat agacagatcg  14100

ctgagatagg tgcctcactg attaagcatt ggtaa                            14135
```